United States Patent [19]

Hansen et al.

[11] Patent Number: 4,534,976
[45] Date of Patent: * Aug. 13, 1985

[54] METHOD AND MEANS FOR REPELLING ANIMALS

[75] Inventors: Helge Hansen; Borje Nystrom, both of Stavanger; Eyvin Torneng, Hinna, all of Norway

[73] Assignee: International Flavors & Fragrances Inc., New York, N.Y.

[*] Notice: The portion of the term of this patent subsequent to May 29, 2001 has been disclaimed.

[21] Appl. No.: 519,182

[22] Filed: Aug. 1, 1983

Related U.S. Application Data

[63] Continuation-in-part of Ser. No. 474,588, Feb. 23, 1983, Pat. No. 4,451,460.

[51] Int. Cl.$^3$ .............................................. A61K 31/56
[52] U.S. Cl. ........................................ 514/169; 514/170
[58] Field of Search ........................... 424/238, 243; 260/397.4

[56]          References Cited
            U.S. PATENT DOCUMENTS 4,151,273  4/1979  Riegelman et al. ............... 424/243
4,451,460  5/1984  Hansen et al. ..................... 424/238

OTHER PUBLICATIONS

Merck Index (1976), pp. 376, 1181, 680, 487, and 471.
Chem. Abstracts, vol. 85 (1976), par. 42,278(q).
Chem. Abstracts, vol. 95 (1), par. 3406j.

*Primary Examiner*—Elbert L. Roberts
*Attorney, Agent, or Firm*—Arthur L. Liberman

[57]            ABSTRACT

Described for use as a key ingredient in an animal control composition and more particularly in an animal repellent composition, is the genus of steroids defined according to the structure:

wherein X completes a substituted cyclopentyl moiety and is one of the moieties:

wherein Y represents methylene, carbinol or keto; and
(Abstract continued on next page.)

wherein Z completes a substituted cyclohexyl moiety and is one of the moieties:
  hydroxycyclohexyl;
  ketocyclohexyl;
  ketocyclohexenyl;
  hydroxyphenyl;
  cyclohexenyl; or
  bicyclohexyl and wherein the dashed line represents a carbon-carbon single bond or a carbon-carbon double bond.

Also described are animal control articles consisting of one or more members of the above mentioned steroid genus and imbedded in a compatible polymer.

15 Claims, 26 Drawing Figures

FIG.1A
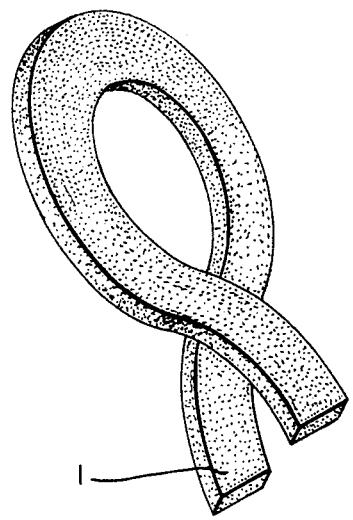
FIG.1B
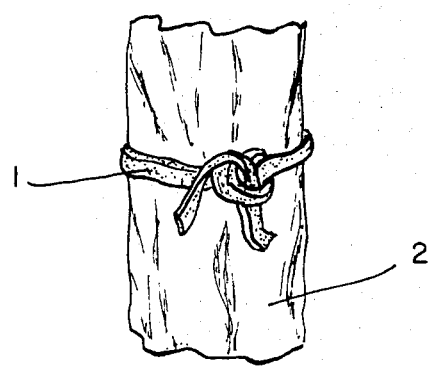
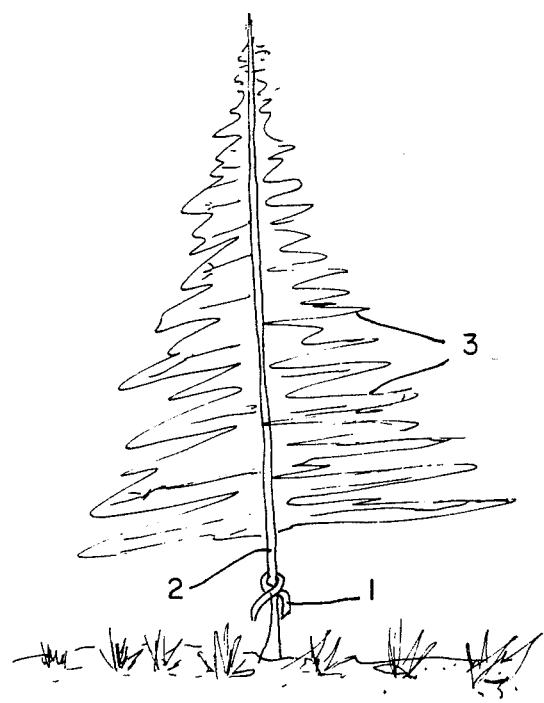
FIG.1C

FIG.1D
FIG.1F
FIG.1E
FIG.1G
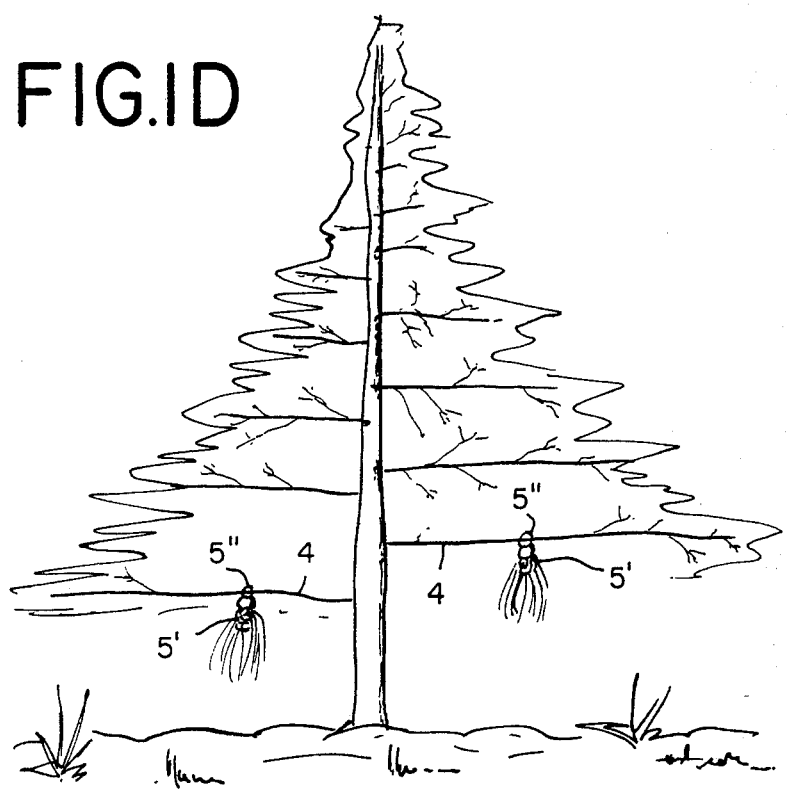
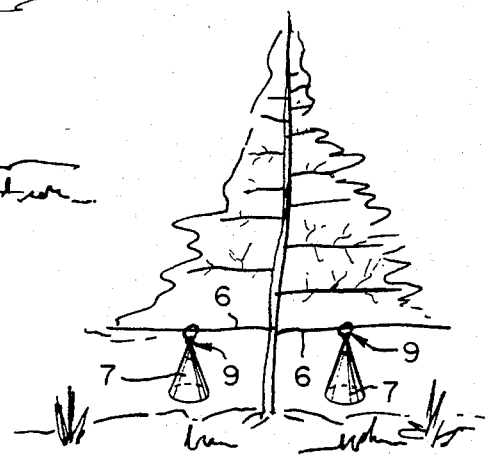
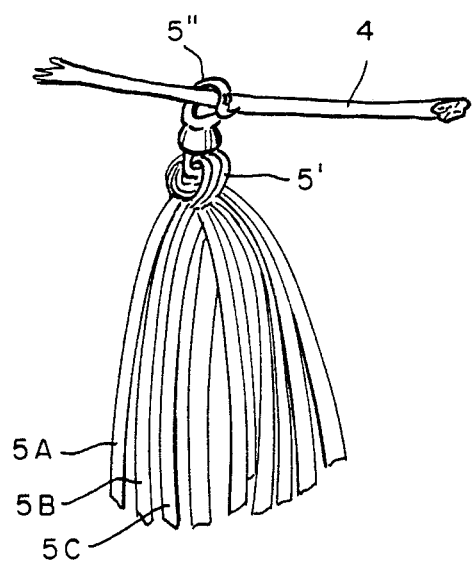
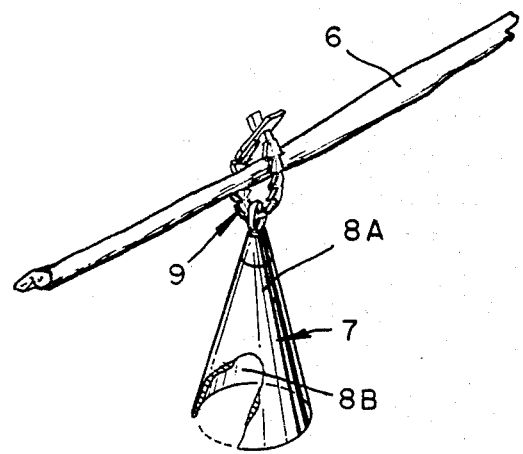

FIG.4
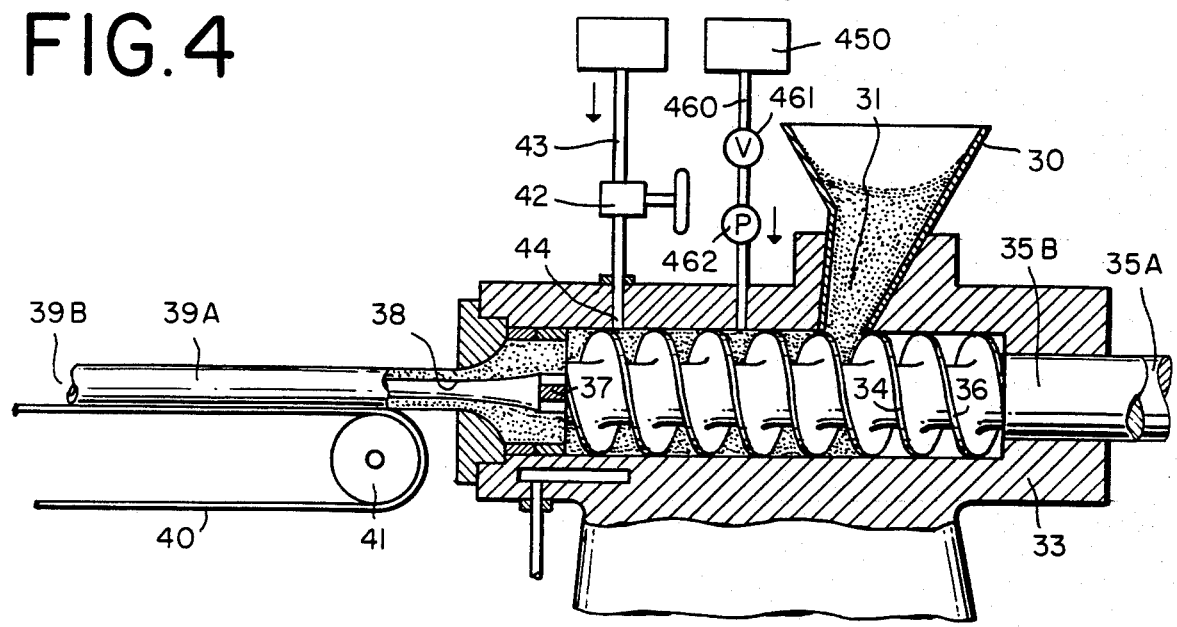
FIG.5A
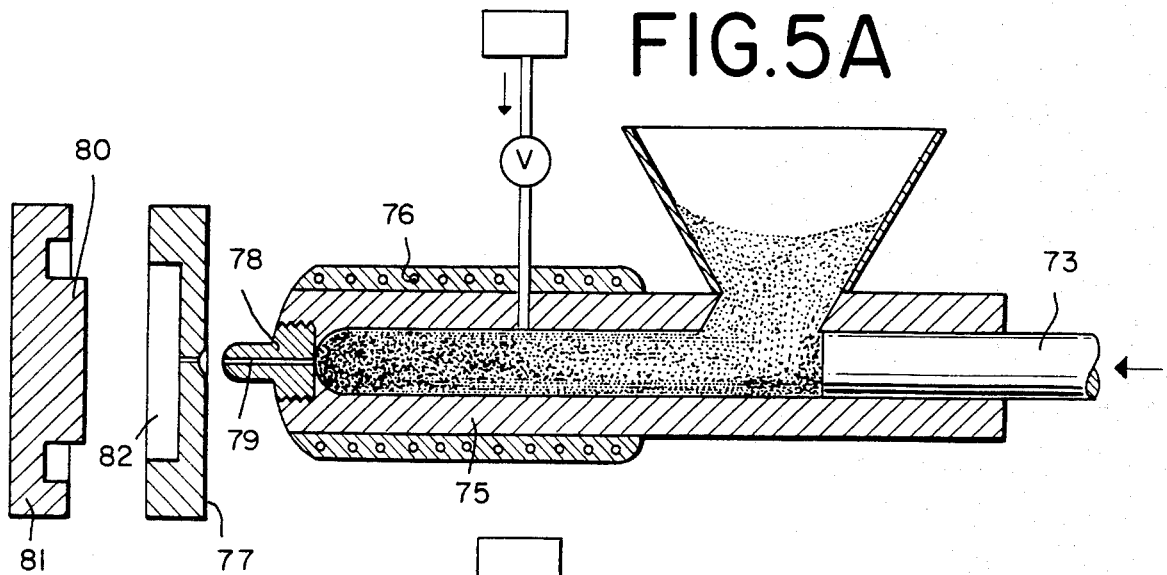
FIG.5B

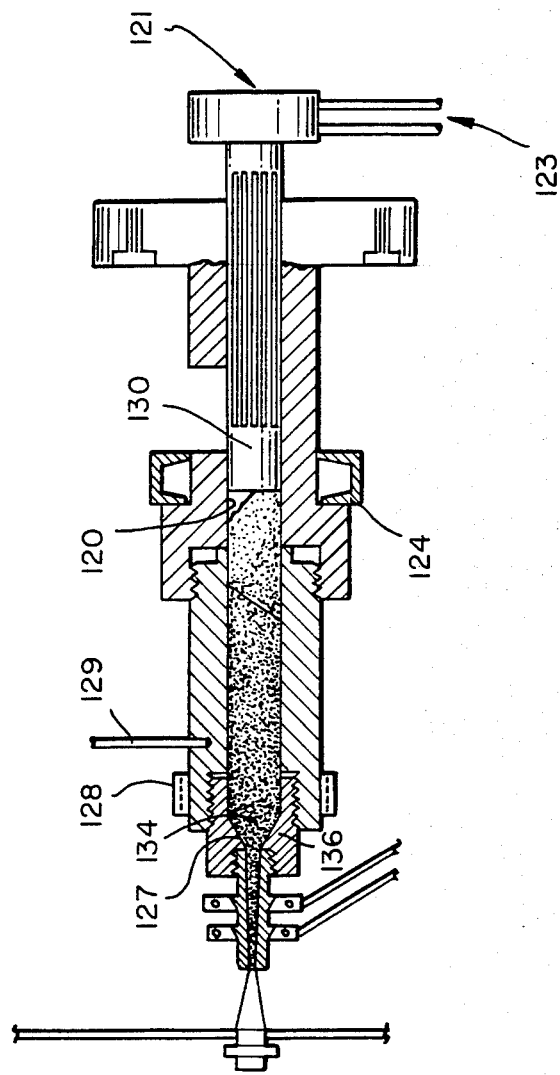

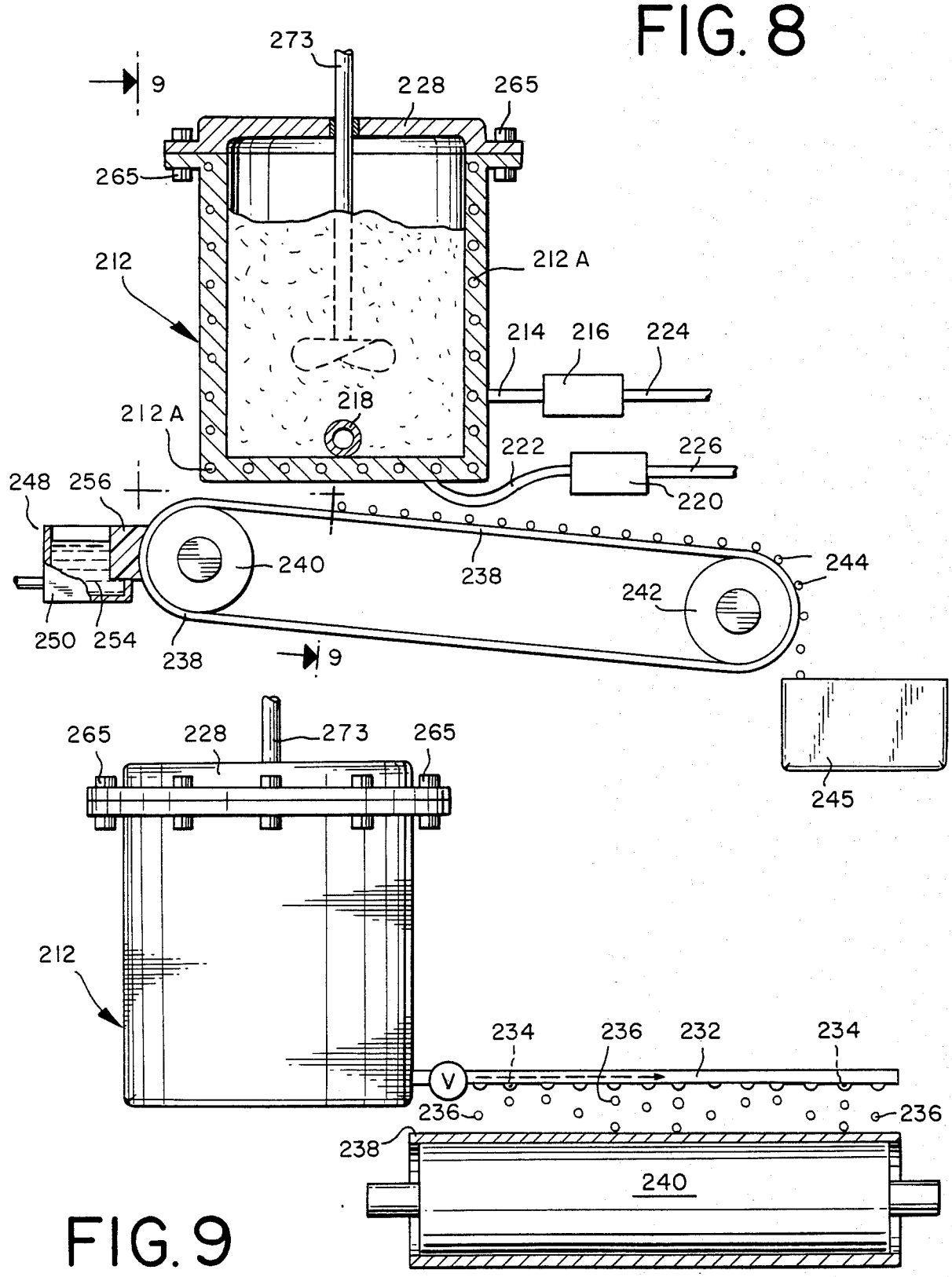

4,534,976

METHOD AND MEANS FOR REPELLING ANIMALS

CROSS-REFERENCE TO RELATED APPLICATIONS

This application is a continuation in part of application for United States Letters Patent Ser. No. 474,588 filed on Feb. 23, 1983 now U.S. Pat. No. 4,451,460 issued on May 29, 1984.

BACKGROUND OF THE INVENTION

This application relates to non-predatory animal control compositions and methods, and more particularly it relates to non-predatory mammalian animal repellent compositions and to methods for repelling such animals, e.g. roe deer, elk, moose and hare.

In modern society conflicts arise between different interests with respect to the use of natural resources such as forests, meadows and fields. The parties in this conflict may be numerous and the individual citizen will often belong to different sides according to the activity exercised at the moment. A rich animal life is important to society in general and particularly gratifying for those interested in hunting, but constitutes a problem to road users and may cause browsing damage in fields, forest plantations and gardens.

The growth in the number of elk, roe deer and rabbits has accelerated recently partly because of various game encouraging measures. At the same time the frequency of accidents caused by collision between such animals as elk and roe deer and cars has become greater and has given rise to rather serious traffic problems (reference: "The Highways Department of the Swedish State: The Game Accident Project", May 1980). Even half-wild, non-predatory animals such as reindeer in the northern part of Scandinavia, cause similar difficulties for the traffic.

Browsing damage by elk, roe deer, rabbits and other non-predatory wild animals on forest plantations, fields and gardens do not involve personal injuries or death but such damage (because of the increase in the population density of said non-predatory animals) has grown to such a size that the damage is significant both from a private and socio-economic viewpoint. Accordingly, a great effort has been made to uncover techniques for keeping such non-predatory animals from the areas which they damage.

A great effort has been made in connection with game and highway traffic regarding the aforementioned problem. Acoustic, optical and chemical methods have been used in addition to the building of fences along certain highways. The optical repellent means, primarily game mirrors, have largely proven to be without effect since after a short familiarization period, the animals are not repelled as a result of the use of said mirrors. By the same token, acoustic methods have been proven to be without effect since after a short familiarization period, the animals are not repelled by the use of said acoustic methods.

If fences are made sufficiently high, they are effective at least insofar as the larger of the non-predatory animals are concerned; such as elk and roe deer. However, for cost reasons and as a result of the fact that the fences hamper outdoor life, this method for avoiding game accidents is impractical (reference: The Highways Departments of the Swedish State: The Game Accident Project, May 1980).

Insofar as the use of chemicals as repellents is concerned, numerous literature exists indicating the efficacy of chemical repellency means against both predatory and non-predatory mammals. Thus, for example, U.S. Pat. No. 3,474,176 issued on Oct. 21, 1969 discloses a method for repelling animals including cats and dogs which comprises exposing such animals to a repellent amount of at least one ketone which is:

(a) a saturated aliphatic ketone having from 7 to 19 carbon atoms;

(b) an unsaturated aliphatic ketone having from 7 to 13 carbon atoms; or (c) 4-t-amyl-cyclohexanone or 4-t-butyl cyclohexanone.

In view of the high volatility of the ketones as disclosed in U.S. Pat. No. 3,474,176, the time of efficacy after treatment of a particular area with the ketones of U.S. Pat. No. 3,474,176 is relatively short and, accordingly, impractical when it is necessary to utilize the repellent material in an outdoor area, e.g. a forest, where it is desired to prevent a non-predatory species from damaging plant life and trees in particular.

U.S. Pat. No. 4,320,112 discloses the use of animal repellents contained in polymers. More specifically, U.S. Pat. No. 4,320,112 issued on Mar. 16, 1982 discloses a receptacle such as a plastic trash can or bag which contains an animal repellent for ridding areas containing the receptacles of annoying insects or for preventing animals from turning over or destroying the receptacles when full. U.S. Pat. No. 4,320,112 discloses the use of effective amounts of naphthalene flakes and oil of citronella added in solid form to the synthetic resin which forms the receptacle.

Furthermore, experiments using other chemical repellent means against various wild animals have been conducted wherein cresol, isobutylalcohol, hartshorn oil, blood meal, thiram and butyric acid have been used as a repellent means against elk. In some cases a certain repellent effect has been observed. However, the experimental results have yielded no definitive conclusions regarding familiarization and other long-term effects (reference: Hans Rosengardten, University of Stockholm, Doctoral Thesis entitled: "Experiments with Smelling Repellents against Elk", January 1979.

It is known that non-predatory animals often react to small of predatory animals attacking the non-predatory animal species whereby the reaction involves escaping by means of running away. Hunters are familiar with the fact that most non-predatory animals avoid contact with human beings and that it is the smell which to a great extent causes the animal to be aware of the presence of human beings. In substantially all cases, when one approaches a browsing roe deer upstream (with reference to air currents) from the roe deer, the roe deer will run away whereas a corresponding attempt downstream (with respect to air currents) will not give rise to any reaction on the part of the roe deer. The tendency of non-predatory animals to run away when noticing human small has been utilized by suspending human hair from trees in order to keep fissiped game away from orchards (reference: "Cultivation of Fruit and Berries", No. 5, 1979/No. 1, 1980, Title: "Non-Poisonous Remedy against Damage by Wild Animals").

Chem. Abstracts, Volume 98, 1983, Number 685a "Neocortical response to odors of sex steroid hormones in the dog" abstracting an article by Onoda, et al, Proc. Jpn. Acad., Series B, 1982, 58(7), 222-5 discloses:

98: 685a Neocortical response to odors of sex steroid hormones in the dog. Onoda, Norihiko; Ariki, Takeshi; Imamura, Kazuyuki; Iino, Mesae (Sch. Med., Gunma Univ., Maebashi, Japan). Proc. Jpn. Acad., Ser. B (1982, 58(7), 222-5 (Eng). In the dog, 24 neurons of a region of the orbital gyrus showed changes in their discharge rate in response to sex steroid and animal product (feces and urine) odors. Of the 24 neurons, 58.3% responded to at least 1 sex steroid tested; testosferone [58-22-0], androsterone [53-41-8], progesterone [57-83-0], or estradiol [50-28-2] and 1 neuron responded exclusively to steroids. In the neocortex, 64.3 and 21.4% of the neurons tested responded to only 1 or 2 steroids, resp. No relation between neocortex response and the sex of the animal was seen. Animal product odors elicited responses in 78.6% of the neurons tested in the neocortex. Thus, in the dog, steroids may act as ectohormones which communicate messages such as sex differences and the sexual state of the animal.

Bullard, et al "Preparation and Evaluation of a Synthetic Fermented Egg Coyote Attractant and Deer Repellent", J. Agric. Food Chem. Volume 26, Number 1, 1978, pages 160-163 indicates that fermented egg will repel deer but attract coyotes. Fermented egg probably contains a small amount of steriods in view of the teachings of:

U.S. Pat. No. 3,741,870 issued on June 26, 1973 (title: "Method of Preparing Δ$^{9(11)}$Estrone") and
U.S. Pat. No. 4,035,236 issued on July 12, 1977 (title: "Process for Preparing 9α-Hydroxy Androstenedione").

The Bullard, et al article is also the subject of Canadian Letters Patent No. 1,022,070, the specification for which is incorporated by reference herein.

Although fermented egg yolk is shown as a deer repellent as shown by Bullard, et al and the said Canadian Letters Patent No. 1,022,070, fermented egg yolk contains thousands of compounds and although it probably contains steroids, there is no reference that infers that it is the steroids in the fermented egg yolk in the concentration indicated that is responsible for the deer repellency. Nothing in the Bullard, et al paper or the Canadian Letters Patent discloses that it is the steroids that are responsible for the deer repellency and up to this point in time, it has been questionable as to whether or not other materials in the fermented egg yolk are responsible for the deer repellency as well as the coyote attractancy.

Furthermore, it should be observed that the ability of non-predatory and predatory animals to perceive smells is usually substantially greater than that of human beings. When substances which affect the olfactory nerve sensitive to aroma are referred to in the preceding and subsequent paragraphs, the perception of predatory and non-predatory animals is referred to. The substances referred to as "smell substances" may sometimes be taken as completely odorless to the less developed sense of smell of human beings. There is reason to believe that the flight reaction of animals, particularly non-predatory animals, in response to the smell of human beings and beasts of prey (e.g. predatory animals) is instinctive and inherited to a great extent independently of previous contact with predatory animals or human beings.

The precise chemical composition affecting human olfaction is largely unknown. However, it may be presumed that there are large variations in olfactory sensitization and sensitivity between individuals and that there are also systematic differences due to age, sex and race. It is known that a large number of various substances may be found in the various secretions from the human body, for instance in sweat and urine. Some of these substances are perceived as odorous by certain persons, whereas others classify them as odorless. However, there are good reasons to believe that there exists a basic structure of smells which characterizes the human being as a species. The compounds in this smell originate from various secretions, primarily from sweat and urine. With respect to sweat, the secretions from the so-called apocrene sweat glands are of special interest. In human beings these sweat glands are present primarily in the axillary regions and in the area around the anal orifice and the genitals. Apart from the direct secretions from the human body, decomposition products also may be formed from these secretions under the influence of air, humidity and microorganisms, especially organisms included in the normal skin flora, and these decomposition products probably form part of the smell specific to the species.

Many of the components found in human sweat and urine have also been demonstrated in other mammals. At least some of the substances which may be expected to form part of the smell specific for the species chemically belong to the group of steroids and many of them have hormonal character. Even the amount of secretion from the apocrine sweat glands is small and the content of steroids in these secretions constitutes a small fraction of the total amount of the order of 0.02%. This amount is, in turn, composed of several different steroids and it may therefore be expected that the amount of individual steroids in secretions from the apocrine sweat glands in human beings is of the order of 1-10 picograms or, in some cases possibly approximately 1 nanogram. Also in the urine, the concentrations of steroids are extremely low, at least if some specific substance such as pregnancy hormones in pregnant females are excepted. The occurrence of steroids in secretions from the apocrine sweat glands which must probably be regarded as the "smell glands" of human beings similar to the corresponding glands in other mammals makes it probable that steroids constitute a significant part of the smell specific for the species. Differences between various mammals with respect to the smell should then be referred to the amount and balance between the various components.

In human sweat and urine the following steroids have been determined.

androst-4-en-3,17-dione having the structure:

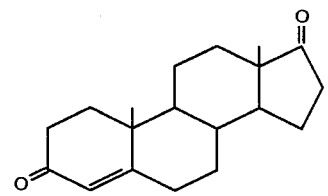

androsterone having the structure:

dehydroepiandrosterone having the structure:

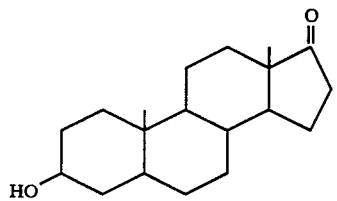

preg-5-en-3β-ol-20-one having the structure:

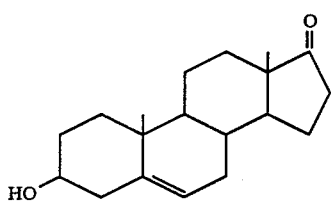

5α-androst-16-en-3α-ol having the structure:

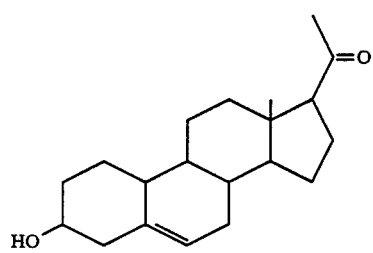

5α-androst-16-en-3-one having the structure:

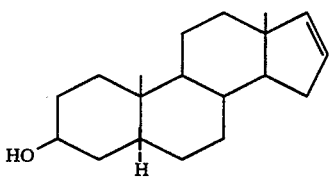

testosterone having the structure:

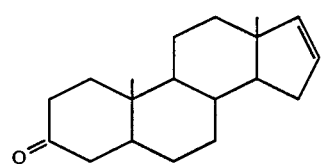

11-keto-aetiocholanalone (3α-hydroxy-5β-androstan-11,17-dione) having the structure:

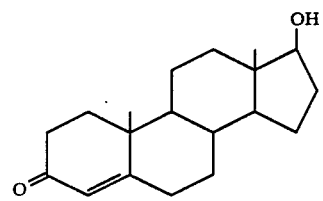

iso-androstanalone (6-β-hydroxy-3,5-cycloandrostan-17-one) having the structure:

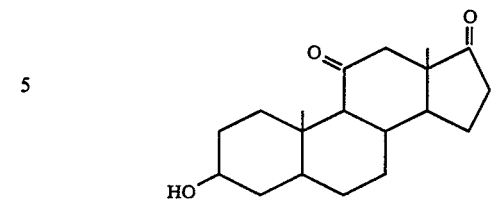

estrone having the structure:

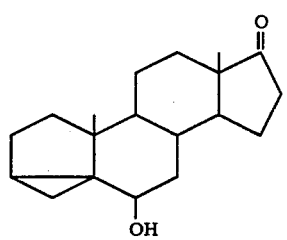

estriol having the structure:

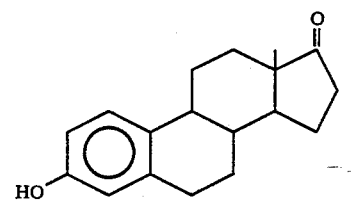

estradiol having the structure:

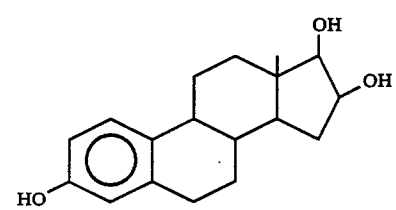

androstan-3-one having the structure:

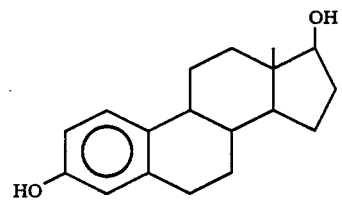

progesterone having the structure:

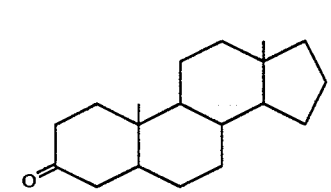

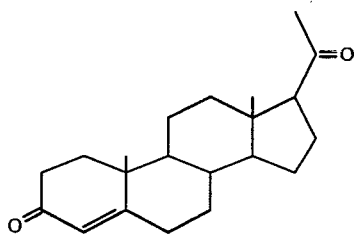

pregnandiol (5β-pregnane-3α,20α-diol) having the structure:

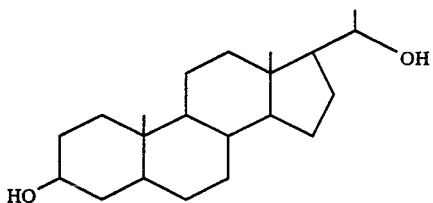

and as oxidation products:
3,5-androstadien-17-one having the structure:

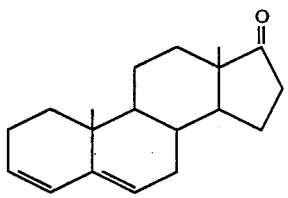

androst-2-en-17-one having the structure:

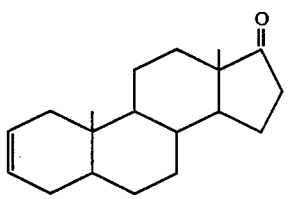

The compound Δ¹⁶-androsten-3α-ol (apocrol) having the structure:

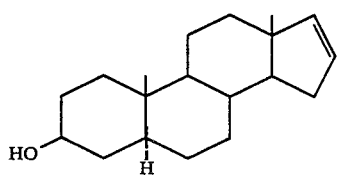

is disclosed by Bedoukian, "Perfumery and Flavoring Synthetics" as having a potential use in perfumery at pages 290 and 291. Similarly, Dr. M. G. J. Beets, "Quelques Aspects du Probleme de L'Odeur" in Parfumerie, Cosmetique, Savon, Volume 5, No. 4, April 1962, discloses "apocrol" as an odorant.

In addition, Patterson, J. Sci. Food Agri., 19, 434, (1968) discloses 3α-hydroxy-5α-androst-16-ene as a musk odor component in boar meat, the 3α-hydroxy-5α-androst-16-ene having the structure:

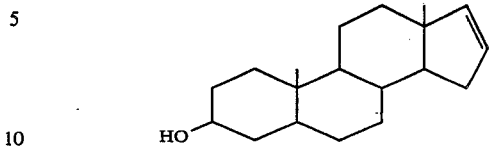

which is apocrol again.

Furthermore, means containing steroids which may be of a hormonal character have been widely used both in medicine and domestic animal care; but not with a view to repelling non-predatory animals.

Accordingly, nothing in the prior art discloses a composition of matter consisting essentially of a steroid and an inert carrier, e.g. a polymer, in which such steroid is embedded the use of which is to repel non-predatory animal species.

OBJECTS OF THE INVENTION

It is accordingly an object of the invention to provide a method for repelling non-predatory animals by placing smelling repellent substances in the area from which the non-predatory animals are to be kept off with the repellent substance being a steroid or a mixture of steroids which are synthetic or which have been extracted from naturally occurring materials and which are of the type occurring on human skin, hair, or in human sweat and urine and/or one or more of the derivatives thereof obtainable by subjecting such steroids to air, moisture or micro-organisms in such a manner as to provide in the environment surrounding the composition, a concentration which is (a) perceptible to the sense of smell of the non-predatory animals and (b) repels the non-predatory animals from the environment surrounding the composition.

It is a further object of this invention to provide articles of manufacture which can be used in a practical manner to carry out the aforementioned first objective.

It is a further object of this invention to provide a process for preparing the aforementioned compositions and articles of manufacture.

BRIEF DESCRIPTION OF THE DRAWINGS

FIG. 1A shows in perspective view a plastic article of manufacture of our invention in the shape in which it would be used after impregnation of such polymer with the steroid animal repellent composition of our invention.

FIG. 1B shows a section of a tree trunk having the article of manufacture of FIG. 1A secured on the circumference of said tree trunk.

FIG. 1C is a schematic diagram of a tree having the article of manufacture (the plastic strip containing steroid animal repellent composition therein) secured about the circumference of the tree trunk.

FIG. 1D is a schematic diagram of a tree having another embodiment of the article of manufacture of our invention comprising a group of several thin plastic strips containing the steroid animal repellent composition therein, secured in a hanging position from a branch of a tree.

FIG. 1E is a close-up view of the article of manufacture illustrated in use in FIG. 1D secured to the branch of a tree.

FIG. 1F is a schematic diagram of a tree having another article of manufacture (a cone having an outer aluminum coating and containing an inner plastic film which, in turn, contains steroid-containing animal repellent composition therein) suspended from a branch of a tree.

FIG. 1G is a close-up view of the cone of FIG. 1F suspended from a tree as shown schematically in FIG. 1F.

FIG. 4 is a cut-away side elevation view of extrusion apparatus used for extruding thermoplastic polymeric tubing containing within the wall of the tubing the steroid animal repellent composition of our invention.

FIGS. 5A and 5B represent cut-away side elevation views of injection molding apparatus prior to and during the injection molding operation for the injection molding of steroid animal repellent composition-containing polymeric pellets produced according to the process of our invention.

FIG. 5A shows the apparatus immediately prior to the carrying out of the injection molding process and FIG. 5B shows the apparatus during the injection molding process wherein the polymeric pellets are being fused and pushed through the injection molding apparatus orifice into the mold.

FIG. 7 is a cut away side election schematic view of jet-molding apparatus useful in forming articles of manufacture from the polymeric pellets containing steroid animal repellent composition produced according to the process of our invention.

FIG. 8 represents a cut-away side elevation view of another embodiment of apparatus used in forming the steroid animal repellent composition-containing polymer composition of our invention.

FIG. 9 is a front view of the apparatus of FIG. 8 looking in the direction of the arrow.

SUMMARY OF THE INVENTION

Figure 2:
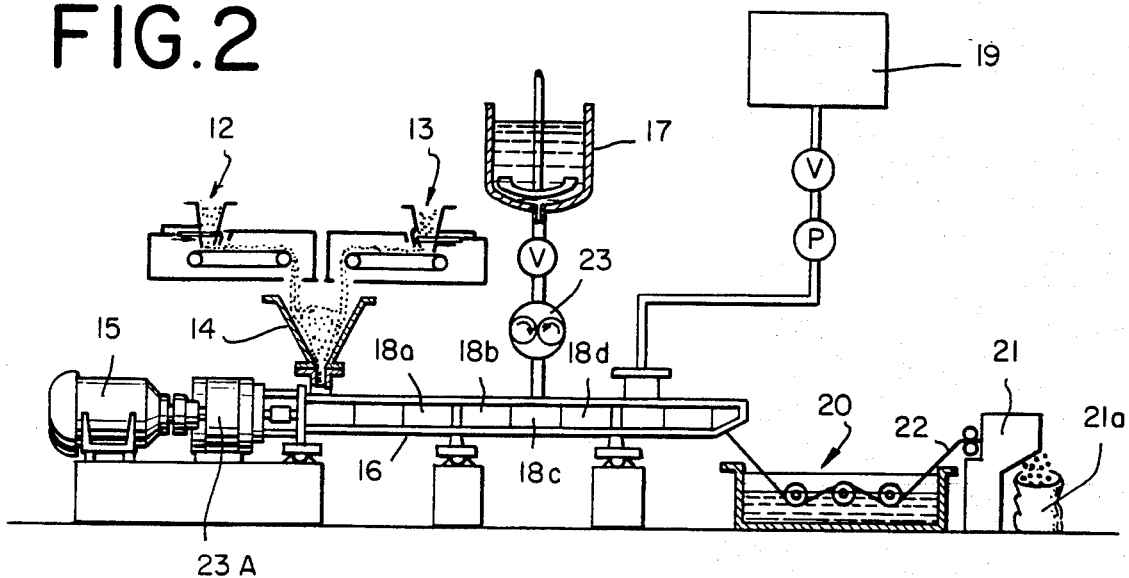
FIG. 2 is a cut-away side elevation schematic diagram of a screw extruder during the compounding of resin with the steroid animal repellent composition of our invention while simultaneously (and optionally) adding foaming agent into the hollow portion of the barrel of the extruder and incorporates pelletizing apparatus used in pelletizing extruded foam tow produced as a result of the extrusion operation.

The present invention relates to a method for repelling non-predatory animals characterized by the use as a repellent substance of one or more steroids which are synthetic or have been extracted from naturally occurring materials and which are of the type occurring on human skin or hair or in human sweat or urine and/or one or more of the derivatives thereof obtainable by subjecting the steroids to air, moisture or micro-organisms in such a manner as to provide in the air a concentration perceptible to the sense of smell of the non-predatory animals.

By way of example and not by way of limitation, such non-predatory animals are:
(i) Species of the genus Cervidae including but not limited to:
  elk;
  roe deer;
  moose;
  caribou;
  reindeer;
  wapiti; and
  musk deer;
(ii) Species of the genus Leporidae including but not limited to hare and rabbits (e.g. of the genus Sylvilagus).

The steroids mentioned above are defined according to the generic structure:

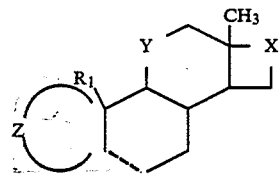

wherein X completes a substituted cyclopentyl moiety and is one of the moieties:

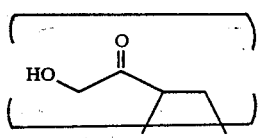

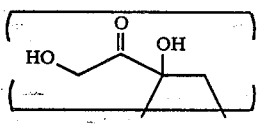

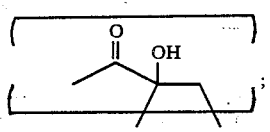

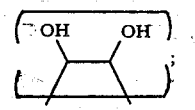

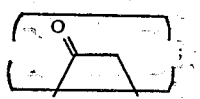

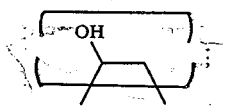

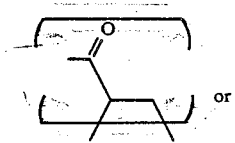 or

wherein Y represents methylene, carbinol or keto; and wherein Z completes a substituted cyclohexyl moiety which is, in the alternative:
hydroxycyclohexyl;
ketocyclohexyl;
ketocyclohexenyl;
hydroxyphenyl;
cyclohexenyl; or
bicyclohexyl
and wherein the dashed line represents a carbon-carbon single bond or a carbon-carbon double bond and include specifically the steroids:

(i) androst-4-en-3,17-dione having the structure:

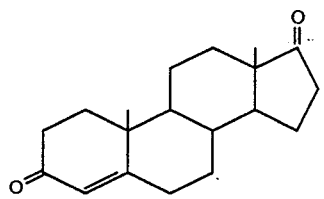

(ii) androsterone having the structure:

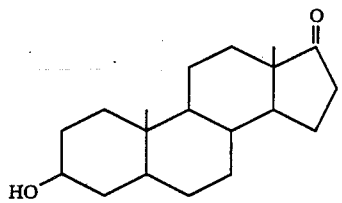

(iii) dehydroepiandrosterone having the structure:

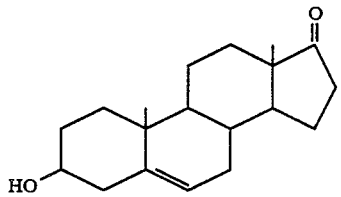

(iv) preg-5-en-3β-ol-20-one having the structure:

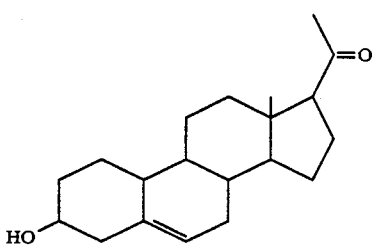

(v) 5α-androst-16-en-3α-ol having the structure:

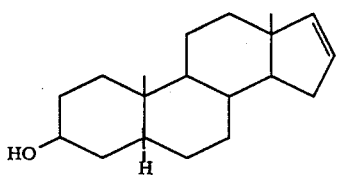

(vi) 5α-androst-16-en-3-one having the structure:

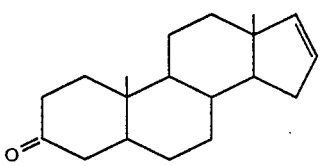

(vii) testosterone having the structure:

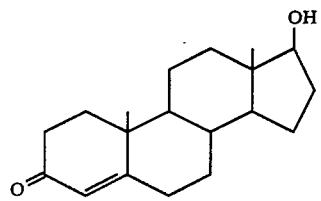

(viii) 11-keto-aethiocholanalone (3α-hydroxy-5β-androstan-11,17-dione) having the structure:

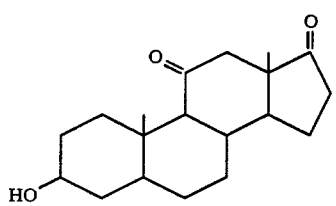

(ix) iso-androstanalone (6-β-hydroxy-3,5-cycloandrostan-17-one) having the structure:

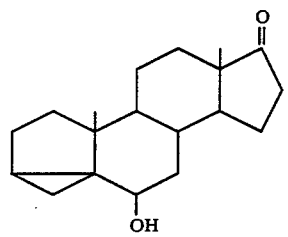

(x) estrone having the structure:

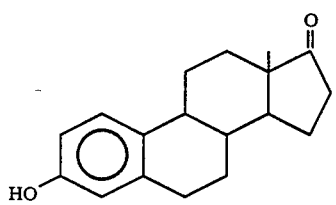

(xi) estriol having the structure:

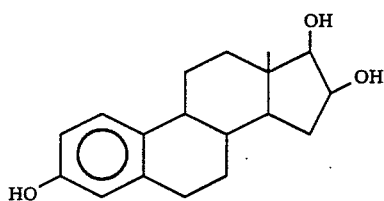

(xii) estradiol having the structure:

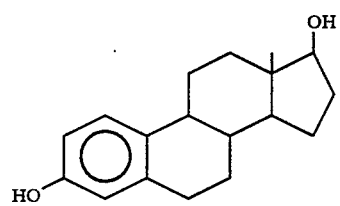

(xiii) androstan-3-one having the structure:

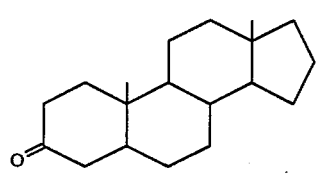

(xiv) progesterone having the structure:

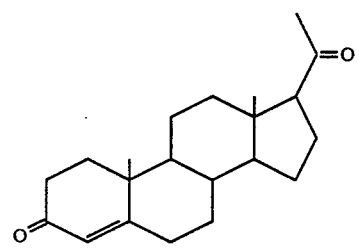

(xv) pregnandiol (5β-pregnane-3α,20α-diol) having the structure:

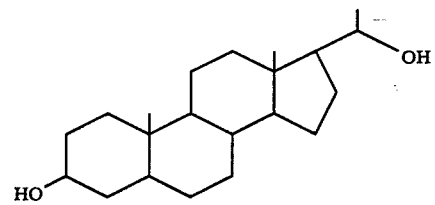

(xvi) 3,5-androstadien-17-one having the structure:

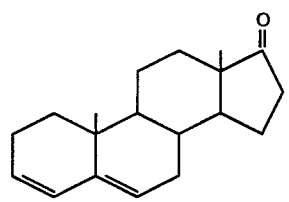

(xvii) androst-2-en-17-one having the structure:

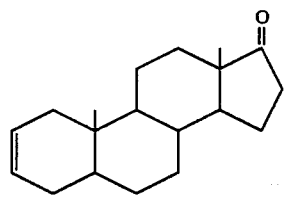

(xviii) corticosterone (11β,21-dihydroxypregn-4-ene-3,20-dione) having the structure:

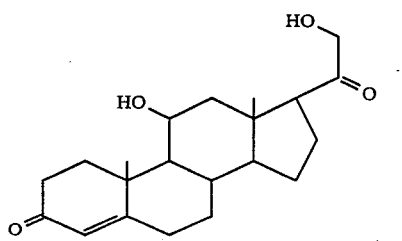

(xix) cortisone (17α,21-dihydroxy-4-pregnane-3,11,20-trione) having the structure:

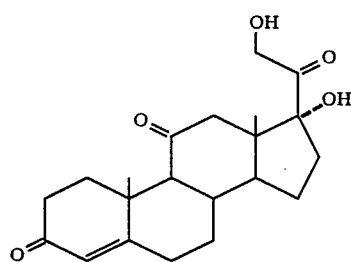

(xx) 21-desoxycortisone having the structure:

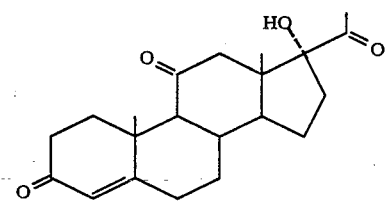

and (xxi) 11α-desoxycortisol having the structure:

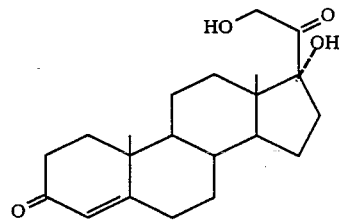

With a view to the complicated composition of the secretions from human smell glands, i.e. dthe apocrine sweat glands, it is surprising that individual components and combinations of a few components of the secretions have proved to exhibit such repellent effects on non-predatory animals comparable to or exceeding the effect of human smell from, for instance, suspended used working clothes and human hair. The substances, the repellent effect of which in this respect have been studied in detail, all chemically belong to the above mentioned generic group of steroids defined according to the structure:

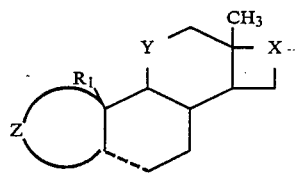

and are synthetic or semi-synthetic substances corresponding to the steroids which have been demonstrated in human skin and hair including body hair or in human sweat or urine.

Individual steroids and compositions containing two or more steroids are well applicable to obtain a repellent effect on such non-predatory wild animals. However, at times the high biological activity of such steroids defined according to the generic structure:

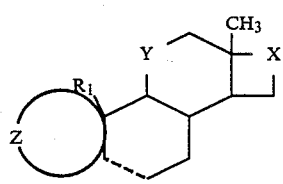

constitutes a handling problem. The high costs of producing steroids also gives rise to the requirement that an attempt must be made to obtain an optimal utilization by controlling the liberation to the atmosphere in a suitable manner. The problems involved in the handling of the steroids and in the control of the liberation to the atmosphere are best solved by combining the steroids or the steroid composition with a carrier into a repellent unit.

The choice of carrier and the design of the repellent unit may be effected in many different ways which are adapted to various conditions of use. However, an essential condition is that the repellent unit, i.e. the combination of the steroid preparation and the carrier, can liberate steroid molecules to the air at a controlled rate so that a sufficiently high and uniform concentration can be maintained in the air surrounding the repellent unit in a desired period.

The invention also provides a means of repelling non-predatory animals characterized in that as a repellent substance it contains one or more steroids which are synthetic or have been extracted from naturally occurring materials and which are of the type occurring on human skin or hair or in human sweat or urine and/or one or more of the derivatives thereof obtainable by subjecting the steroids to air, moisture or micro-organisms and that this repellent substance is combined with a carrier into a repellent unit capable of liberating molecules of the repellent substance into the air for maintaining a concentration perceptible to the sense of smell in non-predatory animals.

It is possible to extract the said steroids and their derivatives from human sweat and urine, but for obvious reasons only synthetic products are used in practice. Raw materials for the synthesis may, for instance, be steroid-alkaloids which may be recovered from certain plant parts or cholesterol. Also fully synthetic methods using petroleum products as starting materials are possible. The methods of the synthesis may be purely chemical, biochemical or microbiological or various combinations of these methods. In some cases it may be advantageous to use an intermediate product from the synthesis, deleting, for instance, the final separation or purification step. Nevertheless, the essential part of the raw material useful in our invention is the steroid defined according to the generic structure:

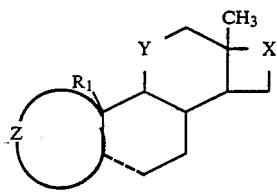

As indicated supra, the naturally occurring amounts of steroids in human secretions are very small. Considering that relatively large molecules are involved, their vapor pressure must be presumed to be very low. However, it is known that the sense of smell of animals and human beings is often so sensitive that no measuring instrument has been produced thus far to date which has the same sensitivity as the mammalian olfactory organs. The experiments carried out to date have not made it possible to establish any lower limit for the amount below which no effect of the said steroids may be observed. However it can be assumed that any such limit lies below the level corresponding to the presence of the steroids in human secretions. For reasons of handling and because of the necessity to maintain a sufficiently high concentration in the atmosphere over a practical period of time, e.g. more than one week, the amounts used cannot be too small. A practical lower limit should be 1 ng of steroid for each repellent unit.

Preferably the amount of steroid defined according to the generic structure:

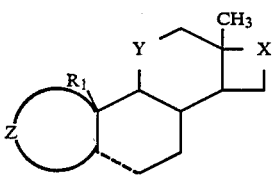

used for each repellent unit should be kept as small as possible for reasons, interalia, including costs. However, there is no indication that relatively large quantities will have negative effects from a technical standpoint. It is therefore not possible to set forth any upper limit of steroid in the repellent article since it would be completely dependent on the location of the steroid containing article of manufacture and the length desired for the overall repellent effect. In preferred embodiments of our invention the steroid amounts have varied between 0.1 μg and 100 mg, preferably between 1 μg and 100 mg for each repellent unit.

The steroids occurring on human skin and hair and in human sweat and urine can at least in part have hormonal properties. When carrying out the present invention, a hormonal effect is an undesired side effect. For this reason it is preferred to use steroids having as small a hormonal effect as possible or to use the steroids in a quantity such that the hormonal effect is made deminimus.

In practical experiments various steroids including the following have been used:

(i) testosterone having the structure:

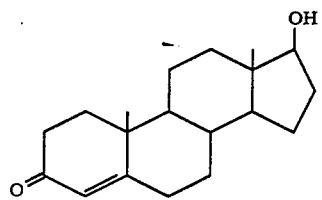

(ii) androsterone having the structure:

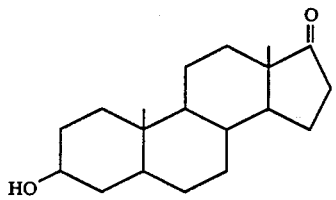

(iii) dehydroepiandrosterone having the structure:

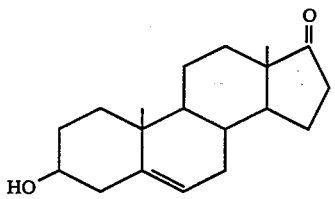

(iv) 11-keto-etiocholanalone (3α-hydroxy-5β-androstan-11,17-dione) having the structure:

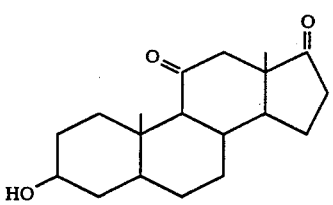

(v) iso-androstanalone (6-β-hydroxy-3,5-cycloandrostan-17-one) having the structure:

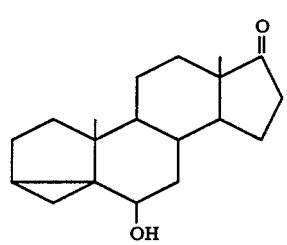

(vi) estrone having the structure:

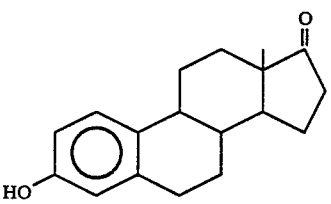

and (vii) androstenol having the structure:

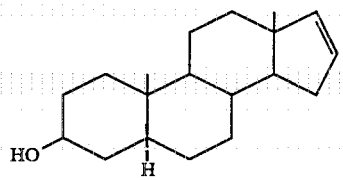

These steroids are the quantitatively most significant in secretions from apocrine sweat glands in male human beings.

Also, the following steroids have been shown to be useful:

11α-desoxycortisol having the structure:

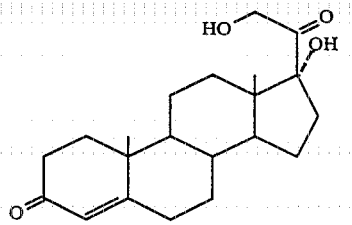

21-desoxycortisone having the structure:

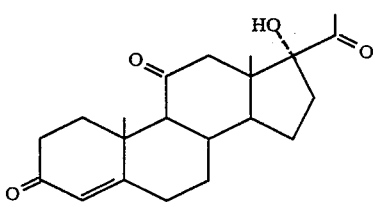

cortisone (17α,21-dihydroxy-4-pregnane-3,11,20-trione) having the structure:

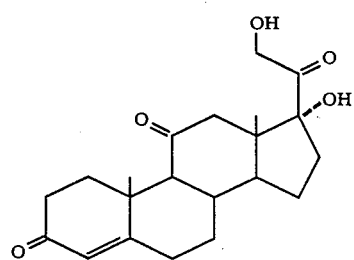

and corticosterone (11β,21-dihydroxypregn-4-ene-3,20-dione) having the structure:

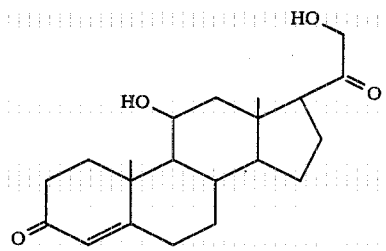

Dehydroepiandrosterone having the structure:

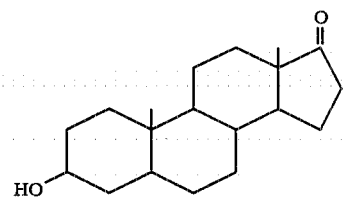

and androsterone having the structure:

combine in relatively low hormonal effect with a very good repellent effect. They may advantageously be used either separately or in combination with each other and/or other steroids. Combinations of two or more steroids are often preferable since they supplement the repellent effect of each other and provide a repellent smell which is closer to the smell of human beings. In this manner, a synergistic effect may be obtained which above all is reflected in a reduced tendency of familiarization. The content of the individual steroids may also be kept lower in the article of manufacture of our invention which reduces the risk of specific hormonal effects in the production and handling. Thus a preferred combination of steroids is a mixture of dehydroepiandrosterone having the structure:

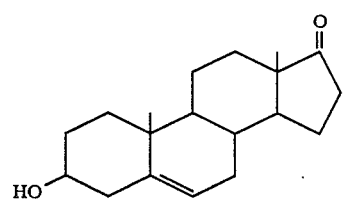

and androsterone having the structure:

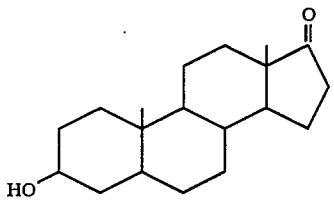

in a mole ratio of dehydroepiandrosterone:androsterone of from about 0.10:0.90 up to about 0.90:0.10.

As stated supra, it is advantageous to combine the said steroids with a suitable carrier when carrying out the invention in practice. One purpose of the carrier is to protect the steroid preparation against loss by mechanical contact. The carrier should further protect the steroids against moisture which may release active substance and lead to inactivation of the repellent effect. However, the most important effect of the carrier is, together with the steroid preparation, to form a combination which liberates steroid molecules to the air at a rate which is controllable to as large an extent as possible.

The combination of carrier and steroid composition is in practical use subjected to very different conditions with respect to temperature, air flow rate, humidity, air pressure and the like. An increase of the air temperature raises the vapor pressure of the steroids, whereas an increase of the air velocity enhances the liberation of active material by reducing the degree of saturation over the preparation. Both effects result in faster consumption of the repellent substance. Whereas an increased liberation of steroid molecules to the atmosphere may be desirable and necessary at increasing wind velocity in order to compensate for the dilution caused by the higher wind velocity, the increase at higher temperatures is pesumably not desirable. It may be convenient to modify the vapor pressure of the steroid composition, for instance, by dilution with some form of solvent which may be present in solid or liquid form. By a suitable choice of diluent, it is also possible to see to it that the liberation at low temperatures is not reduced to unacceptably low values.

Other possibilities of control with the rate of liberation involves controlling the liberation to a larger or lesser extent by diffusion, for instance by making the carrier of a microporous material or by encasing the steroid preparation in a membrane having a limited permeability. Other embodiments in which the diffusion may provide a substantial part of the control mechanism for liberation of repellent substance involve permitting the steroid composition and the carrier to form a gel which may shrink or may not shrink depending on whether or not other components are liberated to the atmosphere together with the steroid molecules.

A further embodiment of our invention for controlling the liberation rate is to use carrier materials having the capacity of absorbing the steroid repellent substance and having a large surface area for each unit of volume, for instance activated charcoal or colloidal or pyrogenic silica. A large number of different methods for controlling the liberation of active steroid substances to the environment are known, and it does not cause substantial difficulties for one having ordinary skill in the art to combine various methods in a convenient manner in order to achieve the desired result.

With respect to the choice of material for the carrier, there are in principle no restrictions. As an example, porous ceramic bodies, native or regenerated cellulose, natural or synthetic polymers of various types in filament form or as microporous or macroporous molds or as gel forming substances may be used. There may, further, be used inorganic materials having a large specific area, for instance certain silica compounds such as zeolites, fine-grained clays, etc. In many cases it is advantageous to use several different materials in combination to obtain the desired result. The technique in this respect is well known to those skilled in the art and is further exemplified infra.

Whereas the steroid preparation and the carrier should be combined in protected environments, for instance in a laboratory or in a manufacturing plant, the final shaping may take place either in direct connection with the combination of the steroid preparation and the carrier or locally when applying it to the final place of application.

In the former case, a molded body is produced which may have any desired shape, for instance tape, strip, sheet, plate, rod, tapering or spherical form. This molded body is advantageously provided with some casing protecting against precipitation and preventing direct contact with the steroid containing body, while still allowing the passage of steroid molecules in vapor form. Further, the casing should be provided with some form of suspension or fastening device or be designed so as in itself to provide a fastening device in order to permit a stable positioning in the place of application. Suitable embodiments include tapes or strips which are wound around tree trunks, posts, etc. and fastened by adhesion, nailing or tieing.

In another embodiment of our invention, the carrier and the steroid preparation are suitably combined to form a viscous liquid or paste which, at the point of application, is applied directly to solid objects such as posts, tree trunks, mountain shelves, etc. The liquid may be applied by being displaced from the container by means of a propulsion gas or by pumping. Another possibility is to effect the application from a tube or a collapsible plastic bottle. In order to avoid the situation whereby individuals involved in carrying out the application are subject to unnecessary inhalation of the steroids, it is convenient to avoid such spray methods in which the material leaves the container as an aerosol, whereas pressure containers or pumps dispensing the liquid material as a foam or a gel can advantageously be used.

When the material is dispensed in the form of a foam, the latter may be of the disintegrating type or of the type forming a permanent macroporous foam structure.

It is often advantageous (when carrying out a local application as set forth supra) to combine with the carrier and the steroid, substances which provide a good adherence to the stationary surfaces on which the application takes place.

Furthermore, the initially liquid or pasty material should have the ability to be transformed into a body which is solid at least on the surface and which can be removed from the substrate only with substantial difficulty. Included in the term "body" are thin films such as lacquer coatings.

It is, of course, possible to apply the combination of the steroid preparation and the carrier by coating with a brush or a filler knife and the like but this method is a less preferred method considering that personnel then has a greater probability of coming in accidental direct skin contact with the steroid preparation and this direct skin contact is to be avoided.

In the case of local application, the term "repellent unit" is intended to cover application of the steroid and carrier "spot-wise" or "dot-wise".

If the area to be protected against intrusion by non-predatory wild animals, e.g. deer, elk or rabbits is very small, for instance a small number of fruit trees in a garden in a residential district (of the order of 1 acre or less), it may be sufficient to apply one repellent unit to a fence post or tree. The size of such repellent unit would be between 0.5 inches and 3 inches in width; 0.5 mils up to about 20 mils (0.0005 inches up to about 0.02 inches) in thickness; and between about 1 and about 5 feet in length.

In most cases, however, larger areas are involved such as forest plantations, large orchards, automobile highways and railroad road beds. In these cases, a relatively large number of repellent units must be placed along the boarder of the area in question. The largest possible distance between the repellent units is then determined by the strength of the preparations (concentration of active steroid ingredient in the polymer, for example, or in polymer-containing articles such as those set forth in FIGS. 10, 11 and 12) and a balance must be found between the desire to have as few units as possible and the amount of steroid which may safely be placed in a repellent unit.

Other factors which also influence the choice of the distance between the repellent unit and the necessary amount of repellent substance in each unit are (i) expected normal wind velocity; (ii) ambient air temperature; (iii) humidity; (iv) requirements for high security against tampering; (v) the required time of protection and (vi) the period of time between replacing of repellent units.

The distance between repellent units may, in extreme cases, be less than 1 meter or more than 100 meters. Preferably the most suitable distance between repellent units is between 5 and 50 meters; usually between 10 and 30 meters. When the substance is applied locally, the shortest of the distances referred to above is often preferable (10–30 meters) since it does not substantially increase the effort if more units are placed in the location.

At "low" and "medium" wind velocity (e.g. 5–20 mph), the flow of air is laminar and parallel to the ground. The liberated steroid molecules substantially follow the flow of air and move relatively slowly in a vertical direction. For an optimal utilization of the repellent substance, it is therefore convenient to position the repellent units at a level above the ground which is adapted to the animal species to be influenced. Thus, concerning rabbits, 1 to 2' above the ground is adequate. Concerning deer and elk, 5 and 7' above the ground is adequate. Too high a positioning may result in the wind sweeping the steroid molecules away so that they cannot come in contact with the olfactory organs of the non-predatory animals involved. Too low a positioning causes the molecules to come in contact with the ground surface where they are bonded and inactivated before they can come in contact with the olfactory organs of the non-predatory animal. For elk and roe deer, the most convenient positioning in the vertical direction is between 0.5 and 2.0 meters above the ground. It is also within this area that the smell glands of an upright person will be found.

The method of incorporating the steroid animal repellent composition into polymers may be according to the technique, for example, of U.S. Pat. No. 3,505,432 issued on Apr. 7, 1970 (the specification for which is incorporated by reference herein) or U.S. Pat. No. 4,237,498 issued on Jan. 27, 1981, the disclosure of which is incorporated by reference herein.

Thus, a first amount of liquified polymer, e.g. liquified polyethylene, is mixed with one of the steroids defined according to the generic structure:

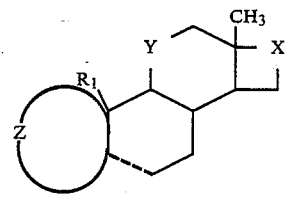

wherein X completes a substituted cyclopentyl moiety and is one of the moieties:

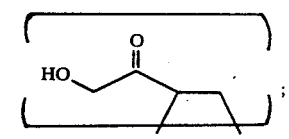

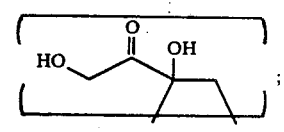

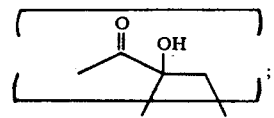

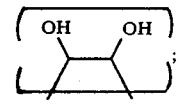

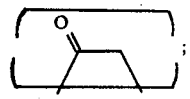

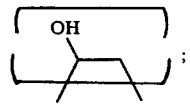

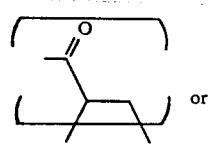

or

wherein Y represents methylene, carbinol or keto; and wherein Z completes a substituted cyclohexyl moiety which is, in the alternative:
hydroxycyclohexyl;
ketocyclohexyl;
ketocyclohexenyl;
hydroxyphenyl;
cyclohexenyl; or
bicyclohexyl
and wherein the dashed line represents a carbon-carbon single bond or a carbon-carbon double bond. Drops are formed from the mixture and the drops are solidified. The solidified drops are then melted, if desired, with a second amount of polymer not containing any animal repellent such as a polyolefin, for example, polyethylene or polypropylene. Usually but not necessarily, the second amount of polymer is larger than the first amount. The resulting mixture thus obtained is solidified subsequent to or prior to ultimate casting into a utilitarian shape, e.g. small spheres which can be placed into a suspendable article such as that illustrated in FIGS. 10, 11 or 12.

Thus, in accordance with another aspect of our invention, the imparting of the animal repellent takes place in two stages. In a first stage, a polymeric material, such as polyethylene, produced, for example, according to U.S. Pat. No. 4,370,455 issued on Jan. 25, 1983, the specification of which is incorporated by reference herein in molten form is mixed with a high percentage of steroid such as 3α-hydroxy-5β-androstan-11,17-dione defined according to the structure:

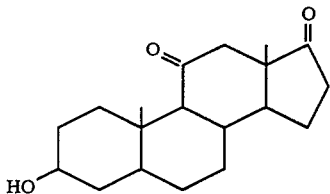

and the mixture is solidified in the form of pellets or beads. These pellets or beads thus contain a high percentage of steroid (e.g. up to 40% by weight of the entire mixture) and may be used as "master pellets" which thereafter in a second stage, if desired, may be admixed and liquified with additional polymers such as additional polyethylene or polypropylene. In addition, additional polymers or copolymers may be used, for example, as specifically described in U.K. Patent Specification No. 1,589,201 published on May 7, 1981, the specification for which is incorporated by reference herein.

In accordance with the present invention, the steroid which may, if desired, be contained in a solvent as a 50% solution (e.g. in tetrahydrofuran, benzyl benzoate or solvents such as those produced according to the process of U.S. Pat. No. 4,165,301 issued on Aug. 21, 1979 and U.S. Pat. No. 4,142,998 issued on Mar. 6, 1979, the specifications for which are incorporated by reference herein) is added to the polymer in a large closed container or drum which is maintained under controlled temperature and pressure condition. While the polyethylene is in a melted condition, it is mixed with the steroid material under agitation. In order that the steroid animal repellent be added uniformly to the polymer, the temperature of the melt is constantly controlled during the process. In addition, it is desirable to carry out the mixing under 2 or 3 atmospheres pressure in order that no solvent or steroid is lost to the atmosphere. The mixture of polymer with the animal repellent is then directed through an elongated conduit or pipe element having a plurality of orifices adjacent to the lowermost portion thereof. The polymer enriched by the steroid animal repellent is permitted to drip through the orifices onto a continuously moving, cooled conveyor upon which the polymer solidifies into small size pellets with the steroid imprisoned therein. The apparatus useful in conjunction with this process advantageously includes a conveyor of a material which will not adhere to the polymer. In order that the droplets form into uniform pellets or beads, the conveyor is continuously washed with a liquid such as water to maintain the surface relatively cool. The pellets are delivered by the conveyor into a container and packaged for shipment.

In the alternative, microporous polymers, e.g. polyethylene, may be formed in accordance with the processes set forth in U.S. Pat. No. 4,247,498 issued on Jan. 27, 1981, the specification for which is incorporated herein by reference. Using the technique of U.S. Pat. No. 4,247,498, microporous polymers, e.g. polyethylene or mixtures of polyethylene with acrylic resins in forms ranging from films to blocks and intricate shapes, are characterized by relatively homogeneous three dimensional cellular structure having cells connected by pores of smaller dimension. The process for making the microporous polymers from the thermoplastic polymers is by heating a mixture of the polymer and a compatible liquid such as a mixture of delta-decalactone, myrcenyl pyridine and trans,trans 4,8-decadiene-2-one in admixture (50:50 mole ratio) with a steroid such as estriol having the structure:

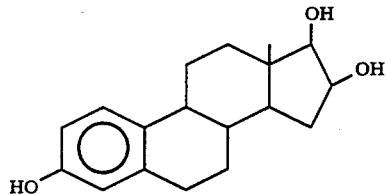

to form a homogeneous solution, cooling the solution under non-equilibrium thermodynamic conditions to initiate liquid-liquid phase separation and continuing the cooling until the mixture achieves substantial handling strength.

According to another aspect of our invention, the polymer resin body is provided which faithfully retains the animal repellent contained therein from which the animal repellent does not exude to a significant extent and which consists essentially of polymer which may be a copolymer of ethylene and a polar vinyl monomer selected from (a) vinyl acetate, (b) ethyl acrylate, (c) methyl acrylate, (d) butyl acrylate and (e) acrylic acid including the hydrolyzed copolymer of ethylene and vinyl acetate. The resulting mixture can contain up to 45% by weight of steroid animal repellent such as estradiol having the structure:

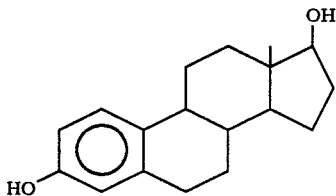

The preferred copolymers are ethylene-vinyl acetate with about 9 to 60% vinyl acetate and ethylene ethyl acrylate with about 6 to 18% ethyl acrylate. These copolymers have been found to work very well with steroid compositions of our invention.

Resins of the type disclosed for use as copolymers are commercially available in the molding powder form. For example, ethylene vinyl acetate copolymers are marketed by E. I. duPont de Nemours Company of Wilmington, Del. under the tradename "ELVAX®" and by Arco Polymer Division under the trademark "DYLAND" and by the Exxon Corporation of Linden, N.J. under the trademark "DEXXON". Ethylene ethyl acrylate copolymers are marketed by Union Carbide Corporation under the tradename "EEA RESINS".

With reference to this additional embodiment of our invention, a process suitable for making animal repellent-resin bodies of this invention comprises heating the polymer mixture until it is sufficient molten to be free-flowing. This is usually between 150° and 250° C. The animal repellent, e.g. mixture of androsterone having the structure:

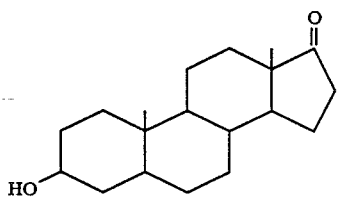

and dehydroepiandrosterone having the structure:

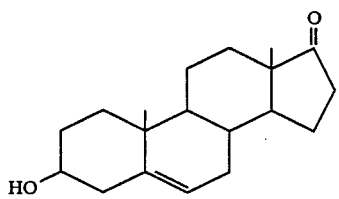

is added to the molten resin and blended through the mass by stirring or other mechanical agitation until a uniform mixture is obtained. A two-roll mill is suited for this purpose. Since each of the resins of the mixture is thermoplastic, solvents are not required for blending but they can be used in order to aid in the mixing. Examples of usable solvents are diethylphthalate, benzyl benzoate and solvents such as those produced according to the process of U.S. Pat. No. 4,165,301 issued Aug. 21, 1979 and U.S. Pat. No. 4,142,998 issued on Mar. 6, 1979, the specifications for which are incorporated by reference herein. The mass containing the animal repellent can be extruded and reduced to molding powder at this point by conventional methods or it can be molded into a desired shape prior to cooling.

Exposure to the melting, blending and molding temperatures of these mixtures of resins does not negatively affect the functionality of the animal repellent.

Molding powder produced as described in the preceding paragraph can be processed through injection or compression molding and the original animal repellent efficacy will be faithfully retained. In fact, the animal repellent efficacy can be faithfully retained for several months storage and in many cases up to a year or more when exposed to extreme atmospheric conditions, e.g. arctic winters or tropical, humid climates such as in the Amazon jungle.

Another aspect of our invention relates to the formation of foamed steroid animal repellent containing polymeric pellets by means of introduction into a single screw or twin screw extruder of, in series, thermoplastic polymer followed by steroid animal repellent taken alone or taken in conjunction with a solvent which is compatible with the thermoplastic polymer and then followed by introduction of a gaseous blowing agent or blowing agent which will produce a gas which is inert to the polymer and to the steroid.

The advantages of using the foamed polymeric particles are multiple, to wit: improved handling; greater retention of animal repellent when not in use; greater length of time during which release of animal repellent from polymer is at "steady state" or "zero order".

The nature of the extruder utilized in the process of our invention to form the foamed polymeric animal repellent-containing polymer particles of our invention may be either single screw or double screw. Thus the types of extruders that can be used are disclosed at pages 246–267 and 332–349 of the Modern Plastics Encyclopedia, 1982-1983 published by the McGraw-Hill Publishing Company, the disclosure of which is incorporated by reference herein. More specifically, examples of extruders which are usable in carrying out the process of our invention (with modification for introduction of animal repellent downstream from the introduction of the polymer and, optionally, with a further modification that the gaseous blowing agent is introduced still further downstream from the point of introduction of the fluid or solid animal repellent) are as follows:

1. The Welex "Super Twinch" 3.5" extruder manufactured by Welex Incorporated, 850 Jolly Road, Blue Bell, Pa. 19422
2. Krauss-Maffei twin screw extruder manufactured by the Krauss-Maffei Corporation/Extruder Division, 3629 West 30th Street South, Wichita, Kans. 67277
3. Modified Sterling model 4000 and 5000 series extruder manufactured by Sterling Extruder Corporation of 901 Durham Avenue, South Plainfield, N.J.
4. CRT ("Counter-Rotating Tangential") Twin Screw Extruder manufactured by Welding Engineers, Inc. of King of Prussia, Pa. 19406
5. The Leistritz Twin Screw Dispersion Compounder manufactured by the American Leistritz Extruder Corporation of 198 U.S. Route 206 South, Somerville, N.J. 08876
6. The ZSK Twin Screw Co-Rotating Extruder manufactured by the Werner & Pfleiderer Corporation of 663 East Crescent Avenue, Ramsey, N.J. 07446
7. The Farrel Extruder manufactured by Farrel Connecticut Division, Emhart Machinery Group, Ansonia, Conn. 06401

8. The MPC/V Baker Perkins Twin Screw Extruder manufactured by the Baker Perkins Inc. Chemical Machinery Division of Saginaw, Mich. 48601

9. The Berstorff single screw, twin screw, or foam extrusion equipment manufactured by Berstorff Corporation, P.O. Box 240357, 8200-A Arrowridge Blvd., Charlotte, N.C. 28224

In producing the foamed or unfoamed steroid animal repellent-containing polymer particles of our invention, various polymers may be utilized, for example, low density polyethylene, high density polyethylene, polypropylene, the copolymer of ethylene and vinyl acetate and polyvinyl chloride. More specifically, the polymers used in the practice of our invention may be copolymers of ethylene and polar vinyl monomer selected from (a) vinyl acetate; (b) ethyl acrylate; (c) methyl acrylate; (d) butyl acrylate and (e) acrylic acid including the hydrolyzed copolymer of ethylene and vinyl acetate. Preferred copolymers are ethylene vinyl acetate with about 9 to 60% vinyl acetate and ethylene/ethyl acrylate with about 6 to 18% ethyl acrylate.

Resins of the type disclosed for use as copolymers are commercially available in the molding powder form. For example, ethylene vinyl acetate copolymers are marketed by the E. I. duPont de Nemours Company under the tradename "ELVAX®" and by the Arco Polymer Division under the trademark "DYLAND" and by the Exxon Corporation of Linden, N.J. under the trademark "DEXXON". Ethylene/ethyl acrylate copolymers are marketed by Union Carbide Corporation under the trademark "EEA RESINS".

The polymer is added to the single screw or twin screw extruder at a feed rate in the range of from about 80 up to about 300 pounds per hour while maintaining the temperature in the screw extruder between about 160° and about 240° C. If the polymer or copolymer powder is added to the extruder at a reference "initial barrel segment", then the animal repellent taken alone or in a solvent or lubricant is added to the extruder under pressure downstream from the addition point of the polymer at 1 or more of "barrel segments" 2-9, barrel segment "1" being the "initial barrel segment".

The animal repellent, e.g. the steroid, e.g. the androsterone having the structure:

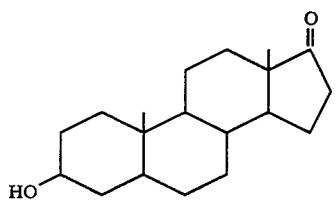

is added as such or in conjunction with a solvent such as a mixture of n-octane and n-nonane, benzyl benzoate, diethyl phthalate or solvents such as those produced according to the process of U.S. Pat. No. 4,165,301 issued on Aug. 21, 1979 and U.S. Pat. No. 4,142,998 issued on Mar. 6, 1979, the specifications for which are incorporated by reference herein, at barrel segments 2-9 of the single screw or twin screw extruder. It will thus be understood that the animal repellent or animal repellent-solvent mixture being added at barrel segments 2-9 must be previously made to be compatible with the polymer added at barrel segment 1 of the single screw or twin screw extruder.

Other polymers useful in the practice of our invention are as follows:

(a) DYLAN® brand of low density polyethylene (DYLAN® is a trademark owned by the Atlantic Richfield Company of Los Angeles, Calif.

(b) DYLITE® brand of expandable polystyrene compositions. DYLITE® is a trademark of the Atlantic Richfield Company of Los Angeles, Calif.

(c) SUPER DYLAN® brand of high density polyethylene. SUPER DYLAN® is a trademark of the Atlantic Richfield Company of Los Angeles, Calif.

(d) Blended polyethylene and carbon black as specifically taught in U.S. Pat. No. 4,369,267 issued on Jan. 18, 1983, the specification for which is incorporated by reference herein.

(e) Polystyrene as disclosed in U.S. Pat. No. 4,369,227 issued on Jan. 18, 1983, the specification for which is incorporated by reference herein.

(f) Polyene/alpha-olefin copolymers as exemplified and disclosed in U.S. Pat. No. 4,369,291, the specification for which is incorporated by reference herein.

(g) Poly-alpha-olefins as exemplified in Canadian Letters Patent No. 1,137,069 issued on Dec. 7, 1982, the specification for which is incorporated by reference herein.

(h) Polymeric compositions as disclosed in Canadian Letters Patent No. 1,137,068 issued on Dec. 7, 1982, the specification for which is incorporated by reference herein.

(i) Poly-alpha-olefins disclosed in Canadian Letters Patent No. 1,137,067, the specification for which is incorporated by reference herein.

(j) Polyolefins described in Canadian Letters Patent No. 1,137,066, the specification for which is incorporated by reference herein.

(k) Polyethylene oxides as disclosed in Canadian Letters Patent No. 1,137,065 issued on Dec. 7, 1982, the specification for which is incorporated by reference herein.

(l) Olefin polymers and co-polymers as disclosed in Canadian Letters Patent No. 1,139,737, the disclosure of which is incorporated by reference herein. Canadian Patent No. 1,139,737 was issued on Jan. 18, 1983.

(m) Polyolefins disclosed in Canadian Letters Patent No. 1,139,738, the specification for which is incorporated by reference herein. Canadian Patent No. 1,139,738 was issued on Jan. 18, 1983.

(n) Chlorinated PVC as disclosed in Polymer 1982, 23 (7, Suppl.), 1051-6 abstracted at Chem. Abstracts 97:145570y, 1982.

(o) Polyepsilon caprolactone co-polymers made by means of alcohol initiated polymerization as disclosed in *J. Polym. Sci.* Polym. Chem. Ed. 1982, 20(2), pages 319-26, abstracted at Chem. Abstracts, Volume 96:123625x, 1982.

(p) Styrene acrylonitrile co-polymers as disclosed in Diss. Abstracts, Int. B, 1982, 42(8),3346 and abstracted at Chem. Abstracts 96:143750n (1982).

(q) Co-polymers of epsilon caprolactone with 1,4-butane diol as disclosed at Kauch. Rezine, 1982, (2), 8-9, abstracted at Chem. Abstracts, Volume 96:182506g (1982).

(r) Polyesters as disclosed in U.S. Pat. No. 4,326,010, the specification for which is incorporated by reference herein.

(s) Chlorinated polyethylene as disclosed by Belorgey, et al. *J. Polym. Sci.* Polym. Phys. Ed. 1982, 20(2), 191–203.

(t) Plasticized polyepsilon caprolactone co-polymers containing dimethyl phthalate plasticizers as set forth in Japanese Patent J81/147844, abstracted at Chem. Ahstracts, Volume 96:69984y (1982), the specification for which is incorporated by reference herein.

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein.

(v) Polyurethane polymers having lactone backbones as disclosed in U.S. Pat. No. 4,156,067 issued on May 22, 1979, the disclosure of which is incorporated by reference herein.

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein.

(x) Resins having polyurethane backbones as disclosed in United States Letters Patent 3,975,350 issued on Aug. 17, 1976, the disclosure of which is incorporated by reference herein.

(y) Low density polyethylene resins prepared according to the procedure set forth in Die Angewandte Makromolekulare Chemie 108 (1982), pages 203–217 (Nr. 1708) [Luft, et al: "Synthesis Conditions and Structure of Low Density Polyethylene"].

Downstream from the addition point of the animal repellent taken alone or in admixture with solvent in the extruder, optionally, a gaseous or liquid containing blowing agent may be added (e.g. at barrel segments 5–10, using the polymer addition barrel segment as a reference barrel segment "1"). Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g. hydrogen, should be avoided since these gases will react with the animal repellent steroid composition and thus alter its efficacy. The pressure of the gas blowing agent being added to the extruder at the point of addition may vary from about 80 up to about 150 psig. Higher pressures may be used without adversely affecting the usefulness of the foamed steroid animal repellent-containing polymer particle.

The feed rate range of animal repellent taken alone or in conjunction with solvent may be between about 0.5% up to about 45% by weight of the polymer.

The die of the extruder may create rod, sheet, film or ribbon. The resulting product may then, if desired, be pelletized to form animal repellent-containing polymer particles which may be foamed or not foamed or the ribbon may be used as is or as a foamed animal repellent polymeric article of manufacture itself.

In addition to the gaseous blowing agents (which are necessarily "inert" gases), blowing agents may be added at the same point on the extruder which will create gaseous voids in the steroid animal repellent-containing polymeric articles of our invention and these "blowing agents" are well known to one having ordinary skill in the art. Examples of such non-gaseous containing materials which yield gases on admixture with the polymer in the extruder but which are still inert to the steroid animal repellent having the generic structure:

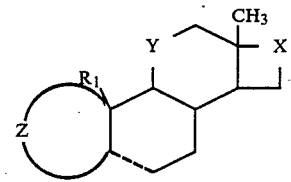

are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein.

(ii) Ordinarily liquid materials such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein.

(iii) Dichlorotetrafluoroethane, tetramethylmethane, monochlorodifluoromethane, dichlorodifluoromethane, and dichlorotetrafluoroethane as specifically described in U.S. Pat. No. 2,948,664 and 2,948,665 issued on Aug. 9, 1960, the specifications for which are incorporated herein by reference.

(iv) Azo bis(formamide); diazoaminobenzene; N,N'-dinitrosopentamethylene tetramine; N,N'-dimethyl-N,N'-dinitrosoterephthalamide; p,p'-oxy-bis(-benzene sulfonyl semicarbazide); azo bis-(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

Figure 10:
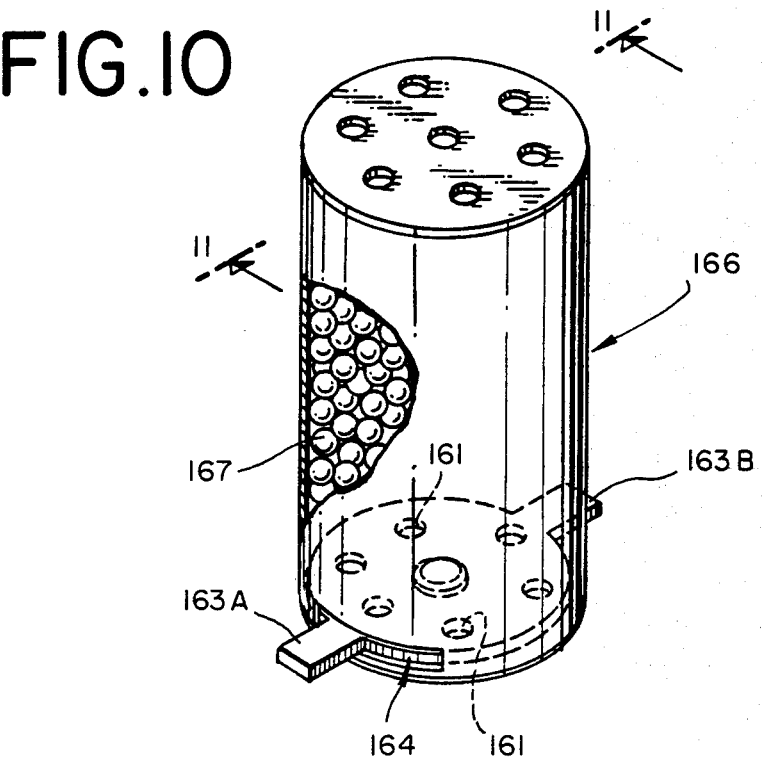
FIG. 10 is a partially cut-away perspective view of an article of manufacture useful as a holding container for steroid animal repellent compositions of our invention, said article capable of being suspended from a tree.
Figure 11:
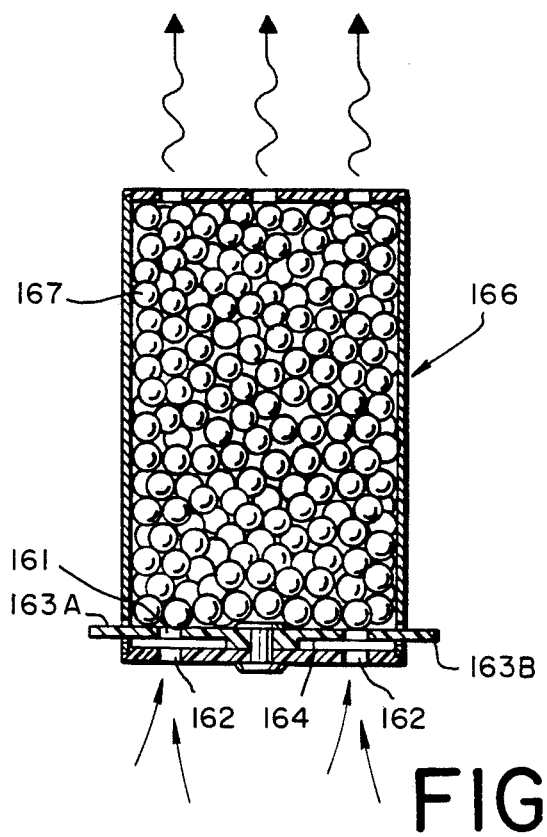
FIG. 11 is a cut-away side elevation view of the article of manufacture of FIG. 10 looking in the direction of the arrows.
Figure 12:
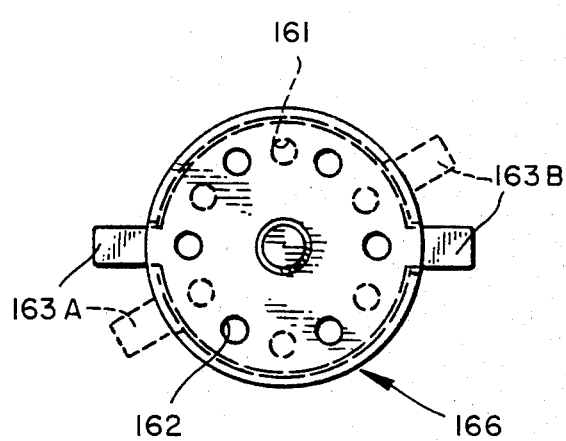
FIG. 12 is a top view of the article of manufacture of FIG. 10.

Polymeric ribbon containing steroid animal repellent shown in FIG. 1A and shown as being used in FIGS. 1B and 1C (as indicated by reference "1") is produced using apparatus shown in FIGS. 2, 3, 4, 5A, 5B, 6 and 7. In addition, articles of manufacture containing steroid-containing polymeric particles as illustrated in FIGS. 10, 11 and 12 may be suspended from the trees at branch 3 as shown in FIG. 1C. The animal repellent-containing polymeric ribbon 1 is wrapped around the circumference of tree trunk 2 as shown in FIG. 1B and in FIG. 1C.

Several polymeric ribbons of lesser thicknesses (and having a much greater surface area) containing steroid animal repellent are shown in FIGS. 1D and 1E. These several ribbons are tied together and the resultant article is suspended from a tree branch 4. Each of the ribbons 5A, 5B, 5C and the like are tied together at 5' and suspended by suspending wire or line 5" from branch 4.

In the alternative, another embodiment of our invention involves the use of a thin polymeric sheet containing steroid animal repellent in the geometric form of a cone 7 as illustrated in FIGS. 1F and 1G. The cone 7 which may be aluminum-coated at 8A has an inner wall of thin polymer coating 8B terminating at edge of the cone 8C. The cone is suspended from its apex by suspending means 9 from branch 6.

In the alternative, the cone may be replaced with a cylinder or frustum of a cone which is coated with the steroid-containing polymer.

The ribbon of FIGS. 1A, 1B and 1C; the thinner strips of FIGS. 1D and 1E and the conical polymeric sections of FIGS. 1F and 1G may be prepared by means of extrusion.

More specifically, FIG. 2 is a schematic cut-away elevation diagram of the extrusion and pelletizing apparatus useful in carrying out a process of our invention during the operation of said apparatus. Motor 15 drives the extruder screws located at 23A in barrel 16, the extruder being operated at temperatures in the range of about 150° up to about 250° C. At the beginning of the barrel, resin at source 12 together with inert additives, e.g. opacifiers, processing aids, colors, pearlescent agents and densifiers at location 13 is added via addition funnel 14 into the extruder. Simultaneously (when the operation reaches "steady state"), steroid, e.g. androsterone having the structure:

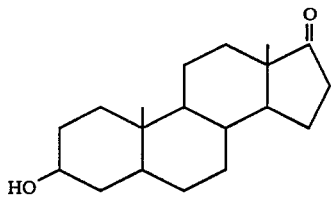

is added to the extruder at one, two or more of barrel segments 3-8 of the extruder (which may be a twin screw or single screw extruder) at locations 18a, 18b, 18c and 18d by means of gear pump 23 from source 17. From source 19 into barrel segments 5-10, if desired, gaseous or liquid blowing agents, e.g. nitrogen, carbon dioxide and the like as described supra, are added simultaneously with the addition of the animal repellent. In addition, the animal repellent may be added in admixture with a suitable inert solvent such as n-octane, n-hexane, benzyl benzoate or solvents such as those produced according to the process of U.S. Pat. No. 4,165,301 issued Aug. 21, 1979 and U.S. Pat. No. 4,142,998 issued on Mar. 6, 1979, the specifications for which are incorporated by reference herein. The feed rate range of resin is about 80-300 pounds per hour. The feed rate range of steroid taken alone or in conjunction with a solvent is 1 to 35% of the feed rate range of the resin. The blowing agent rate range (if indeed a blowing agent is used) is such that the pressure of the gas or the pressure over the liquid being fed into the extruder is between about 50 and 200 psig. If desired, the extruded ribbon or cylinder may be passed through a water bath 20 and pelletizer 21 into collection apparatus 21a. Reference numeral "22" indicates the travel of the extruded material prior to entering pelletizer 21.

Figure 3:
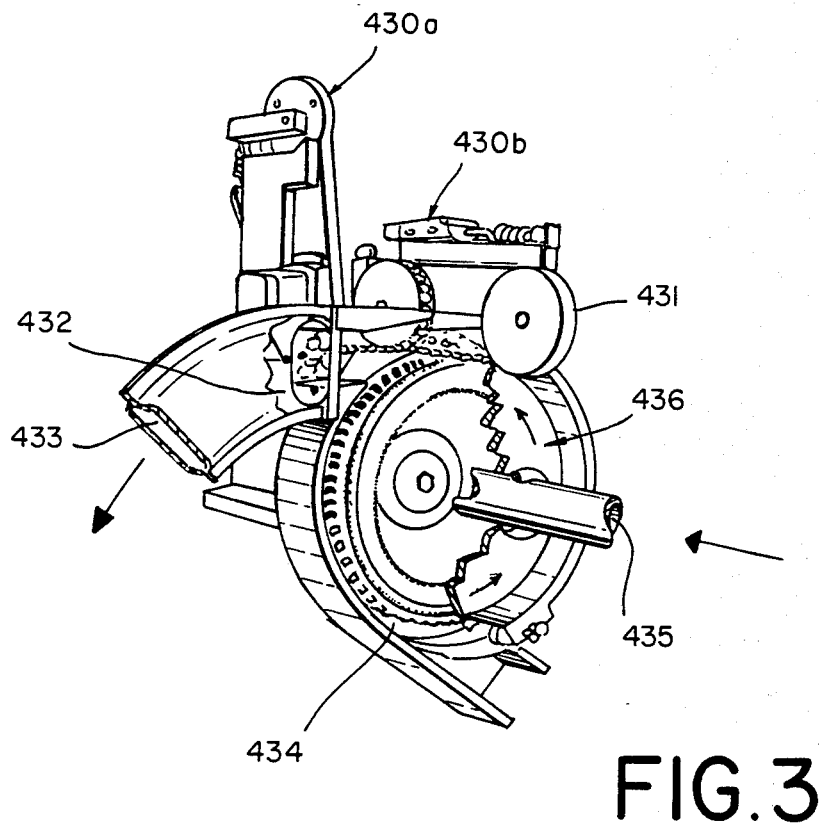
FIG. 3 is a cut-away perspective diagram of a pelletizing apparatus used in conjunction with the extrusion apparatus, for example that illustrated in FIG. 2, whereby the extruded tow is pelletized.

FIG. 3 is a detailed cut-away perspective view of such a pelletizer as is used in conjunction with the apparatus of FIG. 2. The extruded material coming from the water cooler which may already be foamed and which already contains steroid animal repellent is fed into the pelletizer at zero pressure at location 434. The pelletizer is operated using a spinning extrusion die 436 and operated by means of a rotating wheel 434. Moving pellet knife 431 and dual knife units 430a and 430b cause pellets to be formed which fly into a cooling water stream 432. The resulting pellets which may be foamed and contain animal repellent exit from the pelletizer at 433.

Similarly, an extruded tube which can be used as such or cut into smaller lengths is shown to be formed using the apparatus of FIG. 4. Thus, a single screw 35B taken alone or further together with a second screw 35A makes up part of an extruder in casing 33. Resin from resin funnel 30 is fed in at location 31 into the extrusion barrel upstream from the feeding of animal repellent taken alone or in conjunction with solvent which is located at source 450. Simultaneously, animal repellent taken alone or in conjunction with solvent from source 450 is fed through line 460 past valve 461 using pump 462 into the extrusion barrel. The extruder causes an intimate mixing of the animal repellent taken alone or in admixture with solvent in the screw conveyer threads 34 and 36. Simultaneously upstream from the addition point of the animal repellent, optionally, gaseous blowing agent is fed through line 43 past valve 42 into the extrusion screws at location 44. The extruded tube is then forced through die 37 and orifice 38 onto conveyer belt 40 in the form of tube 39A which may be subsequently cut at location 39B. The conveyer belt is operated using roller 41.

The resulting extruded foamed tubing or foamed pellets or non-foamed tubing and non-foamed pellets may be cut up for the purpose of creation of an article of manufacture which contains animal repellent. Such article of manufacture may be molded using injection molding apparatus of the type set forth in FIGS. 5A, 5B, 6 or jet molding apparatus of the type set forth in FIG. 7.

Figure 6:
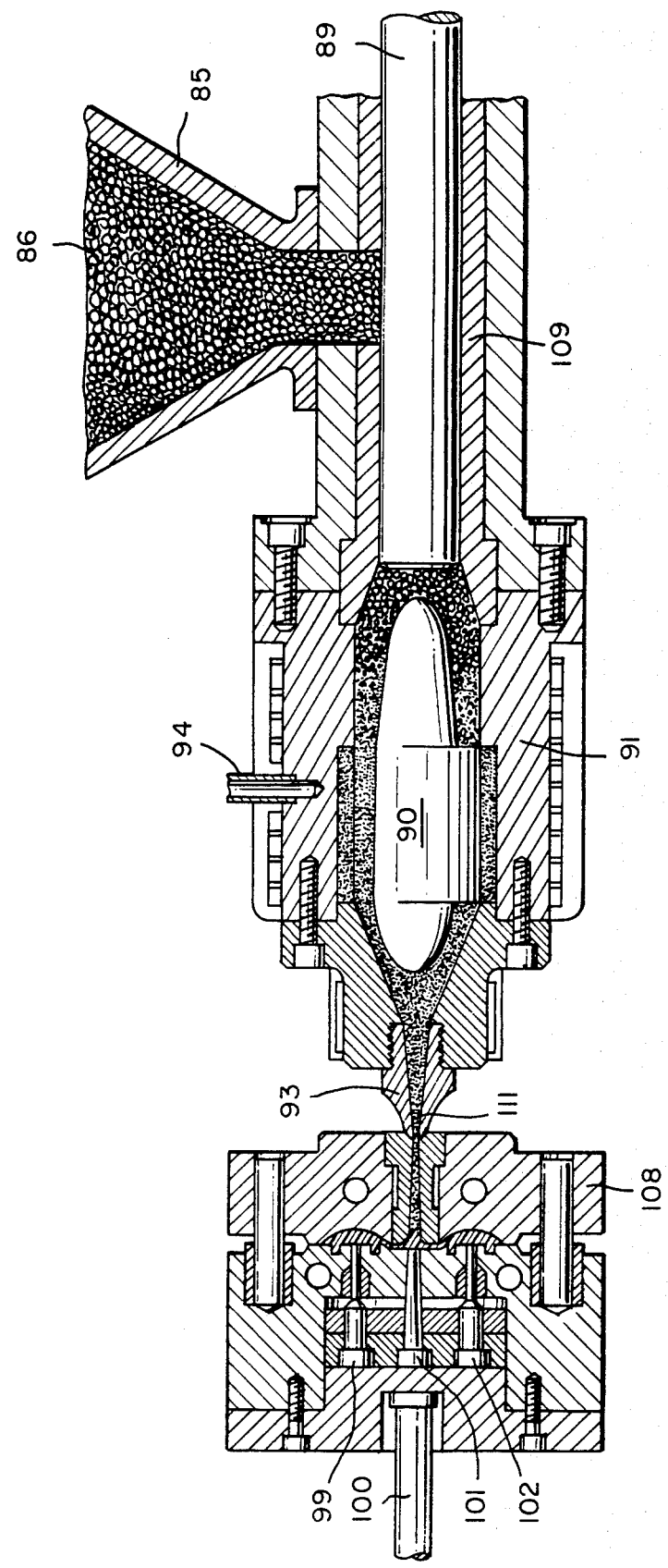
FIG. 6 is a cut-away side elevation view of injection molding apparatus useful in forming articles from the polymeric pellets containing steroid animal repellent fluid or solid composition produced according to the process of our invention.

FIGS. 5A and 5B show the injection molding apparatus in operation. In FIG. 5A, plunger 73 pushes the foamed or non-foamed steroid animal repellent containing polymeric particles through cylinder 75 heated by heating unit 76 through die 78 out of orifice 79 into the mold 77/82/80/81. The mold is composed of a male portion 80 and a female portion 82. Thus, in summary, the injection molding is characterized by the fact that the molding mix is preheated in a plasticizing cylinder having a cylinder liner 109 (as is shown in FIG. 6) to a temperature high enough for it to retain a quasi-liquid condition and is then forced by plunger 89 through the plunger cylinder into heating cylinder 91 (the temperature for which is measured using a thermocouple in thermocouple container 94), into a closed mold 108 which is cold enough to "freeze" the mixture to a solid sufficiently rigid for ejection. Molding mix containing the foamed or unfoamed polymeric particles 86 is fed into the plasticizing cylinder through hopper 85. When the mold opens, the cylinder plunger 89 moves back permitting material to drop into the cylinder. On the closing stroke, the mold members lock tightly together and the cylinder plunger moves forward forcing the newly delivered material from the hopper into the heating zone of the cylinder 90. This material, in turn, displaces a "shot" of molten material through the nozzle 93 into the mold cavity through orifice 111. The mold is cooled so that the shot hardens quickly. Conditions are controlled so that the molten plastic just has time to reach the outermost recesses of the mold cavity before flow ceases. When the mold is opened, the formed piece is loosened by knockout pins 99, 100, 101 and 102. The function of the spreader 90 is to spread the mix into thin films and facilitate uniform heating as it passes toward the nozzle 93.

In FIG. 7 which is a schematic diagram of a cut-away elevation view of a jet molding apparatus useful in producing articles of manufacture using the foamed polymeric animal repellent-containing particles of our invention, the mix is fed into a hopper and from thence falls into a feed cylinder at 120 which is cooled using water cooling 124. The material is then moved forward toward the nozzle end of the cylinder consisting of a nozzle block containing a full taper 127 and heated by a band heater at 128. The amount of heat and rate of heating is measured using a controlling thermocouple 129. The pressure is supplied by the injection plunger 130 having water cooling connection 123 at location 121. Time and temperature must be carefully controlled since the animal repellent steroid must not be decomposed at this point. As the mix nears the nozzle, mild heat is applied. Temperatures of 150°–200° F. are maintained and the mix is merely warmed in this zone. Under the high pressure of the injection plunger 130, the foamed steroid animal repellent-containing particles begins to flow into the nozzle 136 at location 134. Thus, for example, placed around the nozzle are two or more electrodes by means of which intense heat is generated by induction. The heat is transferred to the thin stream of mix as it passes through the nozzle 136. By this means, the temperature of the mix is raised almost instantaneously to 400°–500° F. for a very, very short period of time not enough to convey sufficient heat to decompose the steroid animal repellent. Too high a jet molding temperature can create a destruction of the steroid animal repellent during the production of the animal repellent-containing article of manufacture.

Referring to FIGS. 8 and 9, there is provided a process for forming steroid-containing polymer elements such as pellets useful in the formation of plastic particles useful in fabricating articles such as those set forth in FIGS. 10, 11 and 12. This process comprises heating the polymer such as polyethylene, taken alone or in admixture with other polymers or copolymers having a selected steroid or mixture of steroids contained therein, e.g. androsterone having the structure:

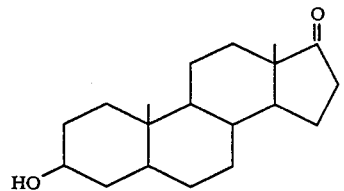

or androst-4-en-3,17-dione having the structure:

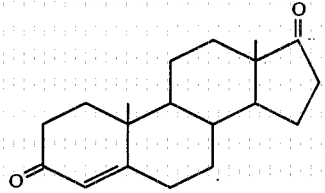

at a temperature in which the polymer remains liquid such as a temperature in the range of 150°–200° C.

The viscosity is in the range of 80–90 Sayboldt seconds. The operating temperature is maintained in the container preferably by electric thermostatic elements which permit a control temperature in the range of 160°–210° C. The lowermost portion of the container is maintained at a slightly lower temperature and the material of the container is taken off at such location for delivery through the conduit and is charged by dropping through the orifices in such conduit.

Thus, referring to FIGS. 8 and 9 in particular, the apparatus used in producing such elements comprises a device for forming a polymer-containing steroid animal repellent taken alone or in admixture with other polymers or copolymers, e.g. polyethylene or polypropylene or polyethylenepolyvinyl acetate which comprises a vat or container 212 into which the polymer such as polyethylene and animal repellent such as androsterone having the structure:

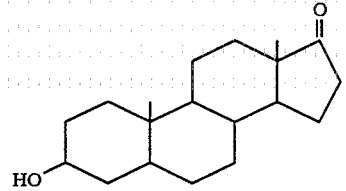

is placed. The container is closed by an air-tight lid 228 and clamped to the container by bolts 265. A stirrer 273 traverses the lid or cover 228 in air-tight manner and is rotatable in a suitable manner. A surrounding cylinder 212 having heated coils which are supplied with electric current through cable 214 from a rheostat or control 216 is operated to maintain the temperature inside the container 212 such that the polymer in the container will be maintained in a molten or liquid state. It has been found advantageous to employ a polymer having a viscosity in the range of between 90 and 100 Sayboldt seconds and having a melting point in the range of 160°–200° C. The heater 218 is operated to maintain the upper portion of the container 212 within a temperature range of 160°–210° C. The bottom portion of the container 212 is heated by means of heating coils 212A regulated through the control 220 connected thereto through a connecting wire 222 to maintain the lower portion of the container 212 within a temperature range of from 150°–250° C.

Thus, the polymer, e.g. polyethylene, added to container 212 is heated from 10–12 hours whereafter animal repellent such as androsterone having the structure:

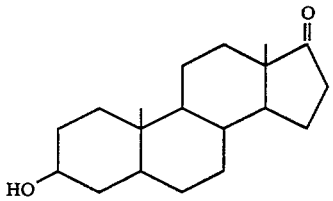

taken alone or in admixture with a high boiling solvent, e.g. diethyl phthalate, benzyl benzoate or solvents such as those produced according to the process of U.S. Pat. No. 4,165,301 issued on Aug. 21, 1979 and U.S. Pat. No. 4,142,998 issued on Mar. 6, 1979, the specifications for which are incorporated by reference herein (for example a 50:50 weight:weight mixture) is quickly added to the melt. The limitation is that the steroid animal repellent and solvent and polymer must all be compatible with one another and in forming the homogeneous melt, one of the constituents must not be evaporated. Generally, about 10–45% by weight of the animal repellent taken alone or in conjunction with a solvent is added to the polymer.

After the animal repellent is added to the container 212 the mixture is stirred for a few minutes, for example 5–15 minutes, and maintained within the temperature ranges indicated previously by the heating coil 212A. The controls 216 and 220 are connected through cables 224 and 226 to a suitable supply of electric current for supplying the power for heating purposes.

Thereafter the valve "V" is opened permitting the mass to flow outwardly through conduit 232 having a multiplicity of orifices 234 adjacent to the lower side thereof. The outer end of the conduit 232 is closed so that the liquid polymer will continuously drop through the orifices 234 downwardly from the conduit 232. During this time, the temperature of the polymer in admixture with the animal repellent and, optionally, the solvent in the container 212 is accurately controlled so that a temperature in the range of from about 150°–200° C. will exist in the conduit 232. The regulation of the temperature through the control 216 and 220 is essential in order to insure temperature balance to provide for the continuous dropping or dripping of molten polymer through the orifices 234 at a range which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid to insure the rapid cooling of each of the pellets 244. The pellets 244 are then collected from the container 245 and utilized in articles as illustrated in FIGS. 10, 11 and 12 which articles may be suspended from the tree of FIG. 1C.

A feature of this aspect of the process utilizing the products produced according to the process of our invention is the provision for moistening the conveyor belt 238 to insure rapid formation of the solid thermoplastic steroid animal repellent-containing pellets 244 without sticking to the belt. The belt 238 is advantageously of a material which will not normally stick to a melted thermoplastic resin, e.g. polyethylene, but the moistening means 248 insures a sufficiently cold temperature of the belt surface for the adequate formation of the pellets 244. The moistening means comprises a container 250 which is continuously fed with water 254 to maintain a level for moistening a sponge element 256 which bears against the exterior surface of the belt 238.

Another feature of this aspect of the disclosure is set forth in FIGS. 10, 11 and 12. In FIGS. 10, 11 and 12 a mass flow control device which can be suspended from a tree is shown. Thus, after placing the polymeric pellets 167 into cylinder 166 (the pellets, for example, being pellets 244 produced according to the apparatus shown in FIGS. 8 and 9) the article which includes mass flow rate accessory 164 with protrusions 163A and 163B is suspended from a tree. Air flows through article 166 past openings 162 of the article and 161 of the mass flow rate control device past pellets 167 through openings 162 back into the environment. Protrusions 163A and 163B can be operated laterally at openings 165 in the articles of FIGS. 10, 11 and 12 whereby the size of the openings 161 can be varied from "no flow" to "full flow" where the openings 161 precisely coincide with the openings 162. In addition such articles may be placed in devices such as those disclosed in co-pending application for U.S. Pat. Ser. No. 377,953 filed on May 13, 1982 (the specification for which is incorporated by reference herein).

Figure 13:
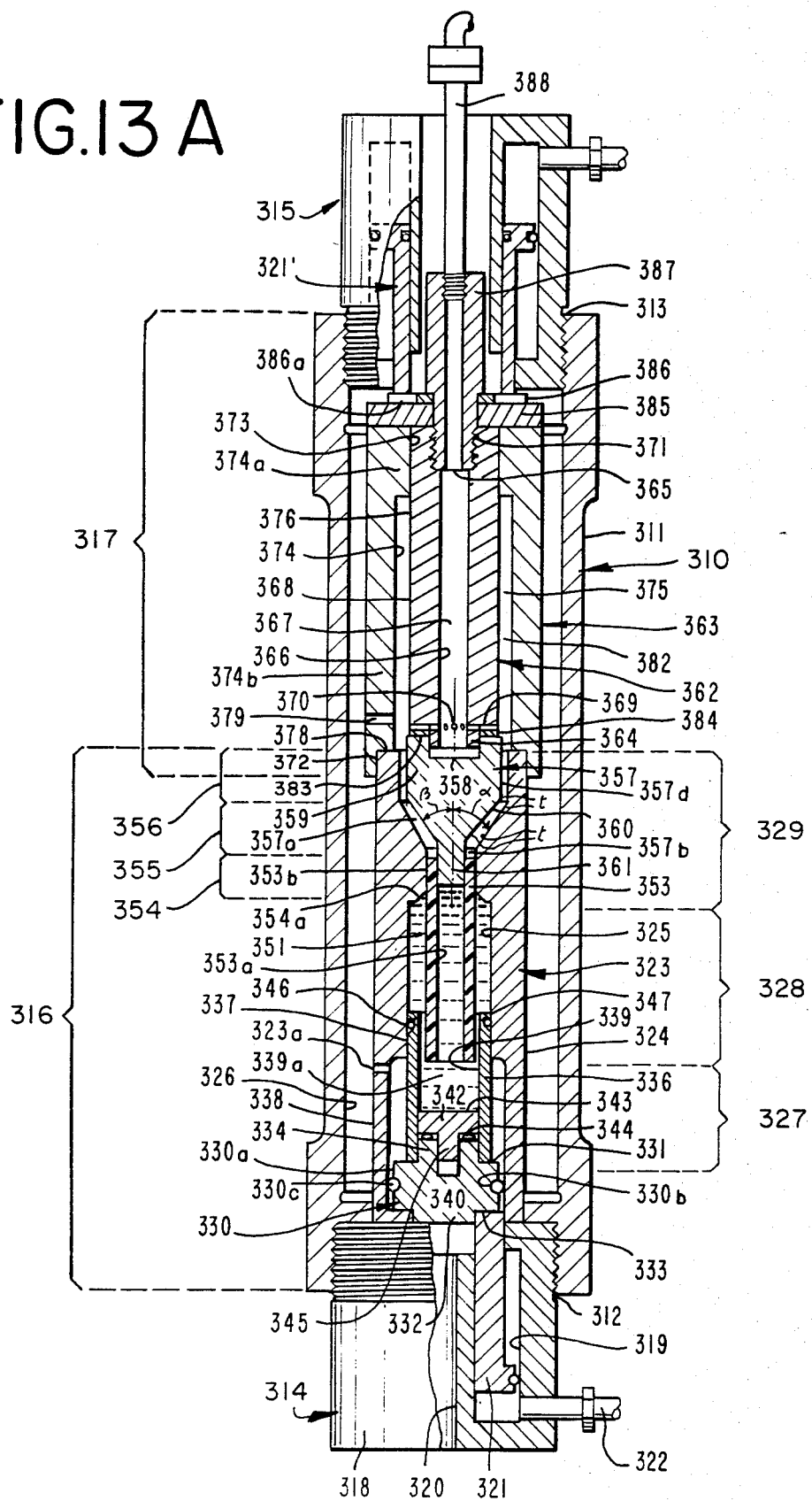
FIG. 13A is an elevation view in cross section of a vertical batch extrusion apparatus which may be used in producing the extruded steroid animal repellent containing polymeric strips of our invention, showing a substantially non-oriented, semi-crystalline heated thermoplastic polymer preform (already containing the steroid animal repellent composition of our invention) in position at the start of the hydrostatic extrusion process.
FIG. 13B is a diagramatic representation of the extrusion of a thermoplastic steroid animal repellent-containing polymer preform into a conduit and the formation of a sheet product from the conduit and showing a pictorial representation of the structure formed in the preform and the conduit.
Figure 13B:
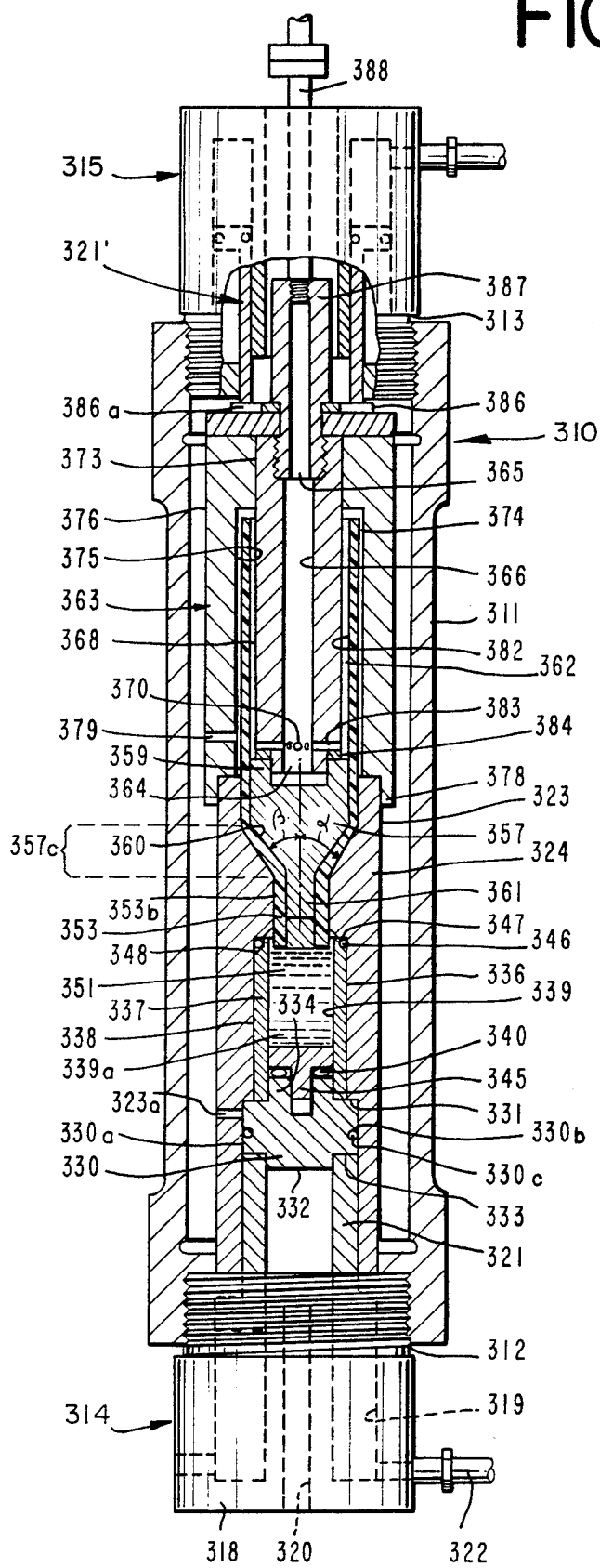

Oriented thermoplastic polymer conduits containing steroid animal repellents of our invention may be produced in a batch extrusion process using an apparatus as shown by way of example only in FIGS. 13A and 13B. FIG. 13A is a cross sectional view in elevation of a vertical hydrostatic extrusion press 310 shown at the start of the extrusion process. FIG. 13B is a cross-sectional view of the extrusion press 310 at the finish of the extrusion process.

The hydrostatus extrusion press 310 comprises a cylinder outer casing 311 having threated open ends 312 and 313, a first hydraulic pressurizing means 314 and a second hydraulic pressuring means 315, a billet container assembly 316 and an extrudate receiving assembly 317 aligned in spaced relationship coaxially within said outer casing 311.

Since pressurizing means 314 and 315 are identical, only means 314 will be described. The pressurizing means 314 is a hydraulic apparatus comprising a cylinder 318 defining an annular chamber 319 with an axial bore 320. A hollow cylindrical piston 321 is positioned in chamber 319 whereby force is transmitted to a cylindrical plug 330 in the billet container assembly 316. Pressure is applied to the piston 321 from a source (not shown) through piping assembly 322.

The assembly 316 includes a cylindrical shell 323 coaxial within outer casing 311. The shell 323 has cylindrical outer surface 324 and a generally cylindrical inner surface 325. A vent 323a is provided in the shell 323 to vent pressure from cavity 326 during extension. The inner surface 325 defines an axial cavity or bore 326 which is divided into a first cylindrical section 327, an intermediate cylindrical section 328 and a third section 329. The first section 327 has a greater cross-sectional area than the intermediate section 328. A generally cylindrical plug 330 having the shape shown has generally parallel upper and lower surfaces 331 and 333, respectively, and a projection 332 extending downwardly from the lower surface 333. The lower surface 333 rests on and is contiguous with the piston rod 321. Extension 332 provides means to center the plug 330 on the piston rod 321. An O-ring 330c in groove 330b of wall 330a provides a friction means for keeping assembly 316 together after it has been assembled and during subsequent heating and insertion into the press 310. The upper surface 331 is provided with a cylindrical projection 334 generally U-shaped in cross-section as shown. A hollow cylindrical piston 336 comprised of metallic wall 337 having an outer surface 338 and an inner surface 339 defining an axial cavity 339a, is supported by plug 330 as shown. A circular elastomer seal washer 340 provides a seat for cylindrical piston head 342 having generally parallel upper and lower surfaces 343 and 344, respectively and also seals hydrostatic fluid 351 into the cavity 339a. A solid projection 345 extending downwardly from surface 343 provides means for centering piston head 342. A sealing O-ring 346 and a support ring 347 generally triangular in cross-section on shoulder 348 of the hollow piston 336 provide sealing means to prevent leakage of fluid 351. The piston 336 is supported on the upper surface 331 of the plug 330. The hydrostatic fluid 351 fills the cavity 339a of the intermediate section 328 and piston 336 and provides means for transmitting pressure to a cylindrical thermoplastic polymer (which has imbedded therein steroid animal repellent) billet 353 in the assembly 316. During extrusion, a very thin film of the hydrostatic fluid 351 is extruded on the surfaces of the billet 353 to thereby provide lubrication for extrusion. The third section 329 is the die of the apparatus 310 and is comprised of a converging conical entrance 354a, a generally cylindrical axial land surface 354, a generally conical diverging wall surface 355 and a generally cylindrical axial land surface 356 substantially parallel to the land surface 354. The land surface 356 may be any length sufficient to aid in setting the extrudate. The diameter of land surface 354 is smaller than the diameter of land surface 356. A mandrel head 357 having a recessed base surface 358, a cylindrical lower portion 359 and a conical upper portion 360 tapering into an elongated cylindrical nose portion 361, is positioned axially within the annulus formed by the die 329. The nose portion 361 is of a size such that when inserted into the bore 353a of the billet 353, an interference fit is produced which is sufficiently strong to keep the mandrel head 357 in position while assembly 316 is being assembled and to maintain the position of the mandrel head 357 during subsequent heating and insertion into the press 310. The outside surface 353b of the billet 353 contacts land surface 354 to thereby form a seal which prevents leakage of hydrostatic fluid 351 during subsequent heating and assembly of the apparatus 310. The surface of die 329 and surface of the mandrel head 357 are spaced a desired distance apart to form an annular orifice or extrusion zone 357a which has a generally converging conical entrance 354a and three zones: a sealing zone 357b formed by the annular cylindrical land surface 354 and the surface of cylindrical nose 361 respectively, a conical expansion zone 357c (FIG. 13B) having a converging cross-sectional area formed by diverging wall surface 355 and the surface of conical portion 360, respectively, and a cylindrical sizing zone 357d formed by the land surface 356 and the surface of portion 359. The transition zones t between the surfaces of the sealing zone 357b and the expansion zone 357c and the sizing zone 357d on the die and mandrel-head, respectively, are provided with curved surfaces having predetermined radii to provide smooth transition areas between any two zones. The angle $\alpha$ that the diverging wall surface 355 makes with the axis of the press 310 may be between 45° and 15° and the angle $\beta$ that the surface of conical portion 360 makes with the axis of press 310 may vary between 50° and 20°. The angle $\alpha$ and the angle $\beta$ are chosen so that diverging wall surface 355 and the surface of conical section 360 will meet if extended, i.e. the annular orifice formed by these surfaces is generally converging and has a converging cross-sectional area while being diametrically diverging. By extruding a thermoplastic polymer (containing steroid animal repellent) billet through the annular orifice shaped as described, the billet is substantially simultaneously expanded circumferentially and elongated axially. It is preferred that the angle $\alpha$ be about 30° and the angle $\beta$ be about 40°. The billet 353 has a diameter which is slightly larger than the diameter of surface 354. When extruded, the outer surface of the billet 353 contacts surface 354 to form a seal which holds the hydrostatic fluid 351 in the assembly 316 to maintain extrusion pressure but at the same time allows a thin film of fluid 351 to be extruded on the surface of the billet 353 to thereby provide lubrication during extrusion. As the billet 353 enters the zone 357c, it is substantially simultaneously expanded circumferentially and elongated axially and flows to the sizing zone 357d. It is possible to vary the axial elongation of the thermoplastic polymer (containing steroid animal repellent) while keeping the circumferential expansion constant by varying the distance between the conical surface of the mandrel-head and wall surface 355.

The extrudate receiving assembly 317 includes an outer shell 363 coaxially within and spaced from casing 311 and a cylindrical hollow mandrell 362 coaxially within shell 363. The mandrel 362 has an open lower end and an open upper end 364 and 365, respectively, an inner surface 366 defining a cylindrical core 367 and an outer surface 368. A shoulder 369 and a plurality of radial orifices 370 extending from inner surface 366 to outer surface 368 are formed in lower end 364. The upper end 365 has a greater cross-sectional area than the remainder of the bore 367 and is provided with threads 371. Outer shell 363 has an open lower end 372 and an open upper end 373, an outer surface 376 and a generally cylindrical inner surface 374 defining a generally cylindrical bore 375. The inner surface 374 has an upper portion 374a and a lower portion 374b. A shoulder 378 is formed on end 372. A plurality of radial orifices 379 extend from the lower surface 374b to the outer surface 376. The upper portion 374a is contiguous with the outer surface 368. The lower portion 374b and outer surface 368 are spaced apart to provide a chamber 382 into which the polymer (containing steroid animal repellent or mixtures of steroid animal repellents) is extruded.

Figure 15:
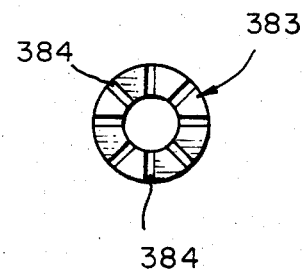
FIG. 15 is a top view of a grooved washer used in the apparatus of FIGS. 13A and 13B.

The mandrel 362 is separated from the mandrel head 357 by a grooved washer 383 shown in FIG. 15. A plurality of radial grooves 384 communicate with the orifices 370 to provide uninterrupted passageways between the bore 367 and the chamber 382.

Figure 14:
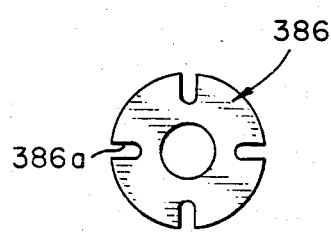
FIG. 14 is a top view of a slotted washer used in the apparatus of FIGS. 13A and 13B.

A circular bearing plate 385 having an outer diameter equal to the diameter of the outer shell 363 and an axial opening having a diameter equal to the diameter of the upper end 365 of the mandrel is contiguous with the ends 374a and 373, respectively. A slotted washer 386, shown in FIG. 14, is inserted beween bearing plate 385 and piston 321' in the hydraulic cylinder 315. A hollow plug 387 and pipe assembly 388 are attached to the mandrel 362 as shown whereby a lubricating and/or cooling fluid may be introduced into the assembly 317. The plug 387 is spaced a distance from piston rod 321' to provide a passage for the lubricating and/or cooling fluid.

To extrude, a semi-crystalline thermoplastic polymer (containing steroid animal repellent) billet 353, for example, isotatic polypropylene containing 15% by weight of a 50:50 mixture of androsterone and dehydroepiandrosterone, is inserted into the shell 323 so that the outer surface 353b of the billet 353 contacts the land surface 354b. The nose 361 of the mandrel-head 357 is inserted into the bore 353a of the billet 353 to make a tight fit. Piston 336 and seal parts 346 and 347 are inserted into section 328. A quantity of a hydrostatic fluid 351, for example, castor oil, is poured into the sub-assembly. The sub-assembly is placed in an oven and is heated to a temperature which is between the 4.64 kilograms force per square centimeter (66 pounds per square inch) heat deflection temperature and 8° C. (14° F.) below the crystalline melt temperature of the polymer (which contains the steroid animal repellent), for example, in the case of polypropylene, the temperature is 129° C. (265° F.) which polypropylene contains the 50:50 mixture of androsterone and dehydroepiandrosterone. Piston head 342 and seal washer 340 are preheated to the same temperature. When at the desired temperature, piston head 342 and washer 340 are inserted into the bottom portion of piston 336. Plug 330 and O-ring 330b also heated to the desired temperature and protrusion 334 is inserted into piston 336 thereby forming assembly 316. The heated assembly 316 is lowered into the casing 311 and is fitted to be contiguous with hydraulic cylinder 314. Assembly 317 is also preheated and is then lowered into casing 311 and is aligned to be contiguous with assembly 316. The mandrel 362 and mandrel head 357 are aligned as shown. Hydraulic cylinder 315 is screwed into place in the open upper end 313. The pipe assembly 388 is placed in position and is connected to a fluid, for example, pressurized air which is introduced into the assembly 317. Hydraulic pressure of about 633 kilograms force per square centimeter (9000 pounds per square inch) is applied by pressurizing means 315 which clamps the press together with 26.6×10⁴N (30 tons of force) and prevents lateral and axial movement of the mandrel head 357 and other tooling in the press during extrusion. Simultaneously, hydraulic pressure is applied to piston 321 in cylinder 314 which in turn transmits the pressure to plug 330 and hollow piston 337 and pressurizes the fluid 351. Initially the fluid 351 and the billet 353 are compressed by the force generated in cylinder 314. When the billet 353 and fluid 351 are fully compressed to a pressure of about 520 kilograms force per square centimeter (7,400 pounds per square inch gauge) or higher, extrusion begins. The pressure remains relatively constant throughout the extrusion time. As noted above, during extrusion a portion of the hydraulic fluid 351 forms a thin film between the surfaces of the billet 353 and the surfaces of the mandrel head 357 and the die 329, respectively, to provide lubrication for the billet as it is being extruded. A lubricating and/or cooling fluid, preferably air at a desired pressure, for example 2.81 to 6.33 kilograms force per square centimeter (40 to 90 pounds per square inch gauge), is fed into the chamber 382 through bore 367 and radial orifices 370. The air forms a flowing film or cushion between the extrudate and the mandrel surface to lubricate the extrudate. The fluid flows along the surface 368, around the extrudate and along surface 374 to radial orifices 379 to cool the extrudate. The fluid then flows along outer surface 376 through the slots 386a in washer 386 and along space between plug 387 and the pressurizing means 315 passes in and out of the apparatus through the top of pressurizing means 315. The use of the lubricating and/or cooling fluid assures a smooth substantially wrinkle-free surface and a substantially uniformly thick wall article. After a time, for example, about one minute, the billet 353 has been extruded and the hydraulic pressure in the hydraulic cylinders 314 and 315 is relieved. Hydraulic cylinder 315 is removed from the press 310. The assembly 317 and the extrudate are removed from the press 310. A portion of the billet remains unextruded and is retained on the mandrel head 351. The extrudate is separated from the unextruded portion by slitting with any conventional known cutting tool such as a slitter knife.

Figure 16:
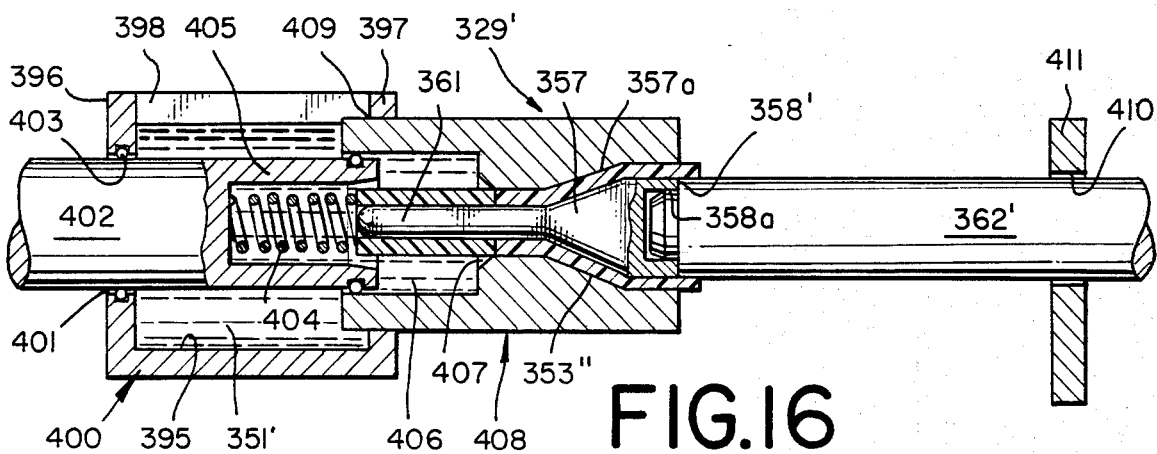
FIG. 16 is a schematic view in cross section of another embodiment of an extrusion apparatus which may be used in a semi-continuous process for hydrostatically extruding a semi-crystalline thermoplastic polymer preform where the preform also contains steroid animal repellent composition of our invention.
Figure 17:
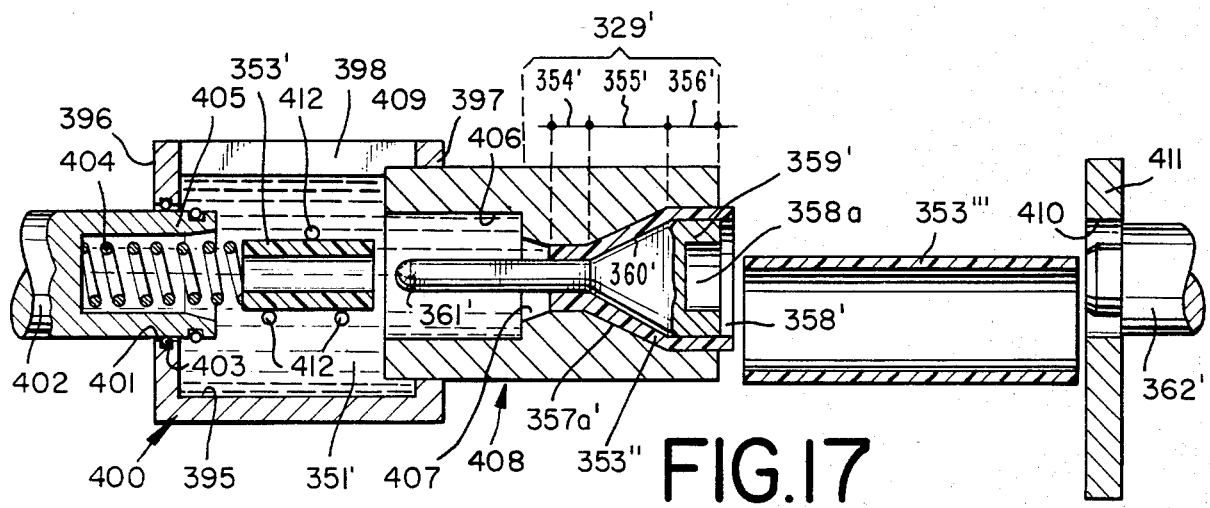
FIG. 17 shows the apparatus of FIG. 16 after the thermoplastic polymer preform containing the steroid animal repellent composition of our invention has been extruded.
Figure 18:
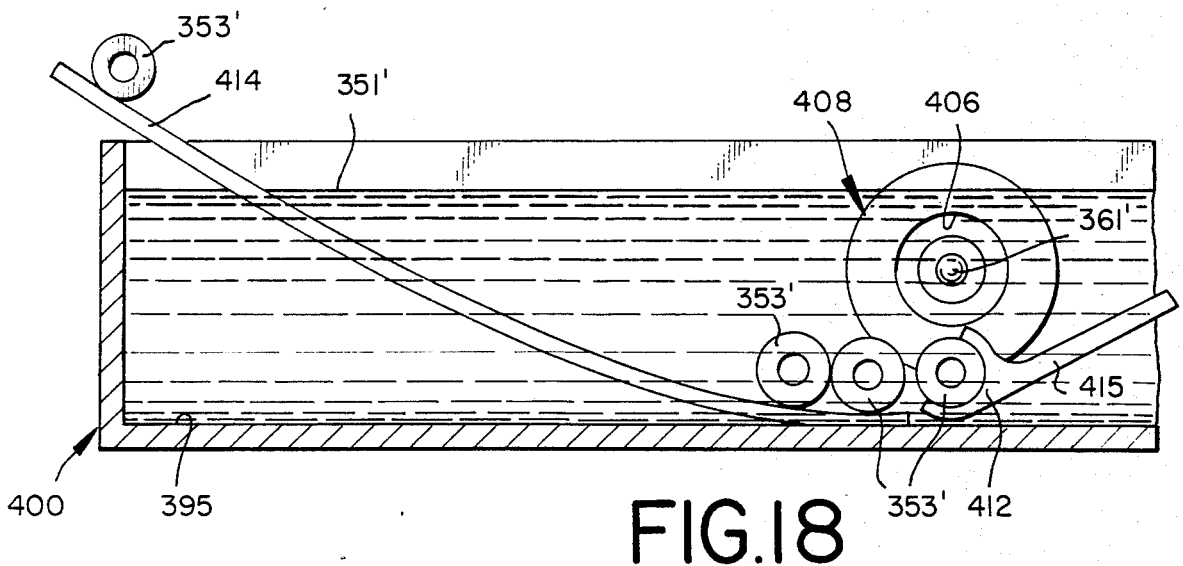
FIG. 18 shows a cross-sectional view of a portion of the heating tank which is used in the apparatus shown in FIG. 16.

While we have shown a batch process, it is also possible to produce the tubular steroid (animal repellent) polymeric product of the invention which is in the form of rods, sheets, and pellets by means of a semi-continuous process using the apparatus which is shown by way of example in FIGS. 16, 17 and 18.

FIG. 16 is an elevation view in cross-section of a press in which a polymer (containing steroid animal repellent) billet is ready to be extruded. FIG. 17 shows the same apparatus as FIG. 16 in which the polymer (containing steroid animal repellent) billet has been extruded and is being ejected from the apparatus. FIG. 18 is an elevation view in cross-section of the fluid tank showing several billets being heated prior to being charged into the apparatus. All of this apparatus is set forth in U.S. Pat. No. 4,363,611 issued on Dec. 14, 1982, the specification for which is incorporated by reference herein.

The extrusion apparatus includes an outer support structure (not shown), a generally rectangular tank 395 with an open top and bounded by two side walls 396 and 397, two end walls 398 and 399 (not shown) and a bottom 400. A hydrostatic and lubricating fluid 351' which is also used to heat billet 353' fills the tank 395.

The fluid 351' is heated by internal or external conventional means, such as a heating coil (not shown), to a temperature which is between the 4.64 kilograms force per square centimeter (66 pounds per square inch) heat deflection temperature and 8° C. (14° F.) below the crystalline melt temperature of the polymer containing steroid animal repellent. Piston 402 is fully movable through opening 401 in wall 396. A seal 403 prevents leakage of hot fluid. One end (not shown) of piston 402 is attached to and activated by hydraulic means. A springloaded cavity 404 in end 405 guides the billet 353' into the rear or pressure chamber portion 406 of axial cavity 407 in die assembly 408. The forward portion of die assembly 408 is a die 329' comprised of a first axial land section 354', a second axial land section 356' and a diverging section 355' connecting the first and second land sections 354' and 356'. Die assembly 408 is mounted in an opening 409 in wall 397. A mandrel head 357' supported by mandrel 362' is axially positioned within cavity 407. The mandrel head 357' has a recessed base surface 358', a generally cylindrical lower portion 359', a generally diverging conical upper portion 360' and an elongated nose 361'. The lower portion 359' and the diverging upper portion 360' and the portion of the nose 361' in cooperation with die 329' define an orifice 357a' which has converging walls but has a generally diverging geometry. The partial extruded billet 353" holds the mandrel head 357' in place during ejection of the product and while heated billet 353' is being placed in position to be extruded. A projection on the front face of mandrel 362' fits into the recess 358a to form a male-female fit whereby any movement of the mandrel head 357' is virtually eliminated. The other end (not shown) of the mandrel 362' is attached to a hydraulic cylinder (not shown). The mandrel 362' is freely movable through an opening 410 in stripper plate 411. The extrudate 353''' is stripped from the mandrel 362' when the mandrel 362' is withdrawn through opening 410 and is rejected from the apparatus. The billet 353' is shown in the fingers 412 of a manipulator (not shown). FIG. 18 is a partial view in cross-section of the tank 395. A sloping ramp 414 as shown allows billet 353' to be fed into the hot fluid 351'. The arm 415 and the fingers 412 of the manipulator may be any type well known in the art.

FIG. 16 shows a billet 353' in pressure chamber 406. Pressure is applied to the billet 353' by piston 402 through hydrostatic fluid 351'. At first, the billet 353' is compressed until a pressure is reached at which the billet 353' begins to be extruded through orifice 357a' onto the mandrel 362'. The billets 353' and 535'' are elongated substantially simultaneously circumferentially and axially. As noted previously, the expansion in the circumferential direction is at least 100% and preferably is at least 200%. The axial elongation may be less than the circumferential expansion but it is preferred that the axial elongation be at least 50% and preferably 100% of the circumferential expansion.

Although a hollow billet and a mandrel head having an elongated nose have been shown, the use of a solid billet and a mandrel head with a sharp needle-like nose and mandrel-heads of various shapes and sizes are well within the scope of operation in this invention as they are in the scope of U.S. Pat. No. 4,363,611, the specification for which is incorporated by reference herein. In all cases the billet must be extruded in the solid state and be substantially simultaneously elongated in both circumferential and axial directions with the circumferential expansion being 100% and preferably 200%.

Set forth below are a number of examples of the use of steroids and repellent units for keeping roe deer and rabbits away from gardens and elk and roe deer and rabbits away from highways. The choice of the animal species and the experimental area are determined entirely by experimental considerations and must not be regarded as limiting, since those skilled in biology will be perfectly aware of the fact that similar effects may be expected in other areas and with other groups of non-predatory animals avoiding contact with human beings and using the sense of smell when adapting to the surroundings. Similarly, it is a matter of course for those skilled in chemistry that other carriers for the steroid preparations will give analogous results provided that the design has been chosen so as to satisfy the previously mentioned requirements of a continuous liberation of steroid molecules to the atmosphere.

EXAMPLE I

Extraction sleeves (hollow cylinders, the walls of which are 0.02 inches thick and the dimensions of which are 30×80 mm) were impregnated with androsterone by an addition of 1 ml of a 1% solution of androsterone.

The repellent units (extraction sleeves) were suspended at intervals of 10 m around an orchard, in which browsing damages caused by royal stag had regularly occurred. In an experimental period of 4 days, no visits of royal stag occurred. The repellent units were then removed and the orchard watched for browsing damages for 4 days. Already the first night the orchard was visited by royal stag which caused browsing damages. These visits were repeated for the subsequent days.

Another experiment, this time with extraction sleeves impregnated with 10 mg dehydroepiandrosterone, was carried out. Again, no sign of royal stag or browsing damages could be observed during a period of 4 days. During a new control period without the suspended repellent units, the stags returned to the orchard already the first night and caused browsing damages. The browsing continued for the subsequent nights.

The experiments were conducted in the mouth of February.

EXAMPLE II

In this case a nursery with large plantations of fruit trees was used for the field experiment. The plantations had frequent visits of both royal stag and roe deer causing substantial browsing damages.

The experiments were conducted in the period February to April. Most of the time the ground was covered by snow so that it was easy to record visits of stag and roe deer in the plantations and their surroundings. Repellent units of the same type as described in Example I were prepared, this time impregnated with 10 mg androsterone and 10 mg dehydroepiandrosterone in combination. The repellent units were suspended at intervals of 10 m around the field. The sleeves were covered by plastic film to protect them against precipitation.

During the first 7 days, there were no records of roe deer or stag in the protected areas. The seventh night, one roe deer entered the area. The tracks showed that the animal had been restless, and that it had soon disappeared without browsing on the fruit trees.

After this observation, there was no recorded visit from roe deer or stag during 38 days.

On the 45th day counted from the beginning of the experiments, tracks were recorded of a stag which had acted similarly to the roe deer previously referred to. Neither animal had browsed on the fruit trees.

The tracks of a herd of 12 to 15 stags and several roe deer regularly appeared in the vicinity of the experimental area during the experimental period, but traces of these animals were not found closer than approximately 100 m from the protected area, except for the two cases referred to above.

After 45 days, the repellent units were removed. Already the first night the plantations were visited by both roe deer and royal stag which caused substantial browsing damages.

EXAMPLE III

This experiment was conducted in a geographically isolated area having a numerous stock of roe deer. In this area, there was an orchard which was the object of browsing damages from roe deer. Because of the geographical isolation and the density of roe deer, there was reason to believe that the normal caution of the animals and the fear of human beings may have been reduced.

Repellent units of the same type as described in Example II were suspended in the outskirts of the orchard at intervals of about 10 m.

The ground within and immediately around the orchard consisted of loose soil which made it easy to record the movements of the animals in the area.

Before the start of the experimental period, visits and browsing damages by 3 to 5 animals each night were recorded. After the repellent units were positioned, no visit of roe deer was recorded for an experimental period of 45 days.

On two occasions during the experimental period, tracks of roe deer were recorded in the vicinity of the orchard. In those instances the animals had approached the protected area in following wind and in high speed, and halted about 25 m from the repellent units and returned in long leaps.

When the repellent units were removed at the end of the experimental period, the roe deer returned already the first night in the same amount as previously with resulting substantial browsing damages.

EXAMPLE IV

This experimental series was conducted in a forest area having a dense population of elk and roe deer. An approximately 600 m long section of gravelled forest road was chosen as an experimental area. By regular inspection, it was possible to register how many animals followed or crossed the road, since it was possible to read the tracks even in dry periods.

In a control period of 6 days before the first repellent experiment there were on the average 5 passages of elk and 2 passages of roe deer each day.

Extraction sleeves impregnated with 10 mg androsterone for each sleeve were suspended on both sides of the road at intervals of about 20 m. During an experimental period of 10 days, no elk or roe deer passed the protected section of the road. By inspecting other sections of the forest road, it was possible to establish that there were still animals in the area.

During a control period of 4 days after the repellent units had been removed, there were on the average 4 passages of elk and 1 passage of roe deer each day.

Corresponding experiments were carried out on the same road section with repellent units impregnated with 10 mg dehydroepiandrosterone, i-androsterone, oestrone, androsterone and 11-ketoaetiocholanalon, respectively. In all experiments, the repellent units were suspended for 10 days, whereas the control period was 4 days as in the first experiment. During the control periods between 3 and 7 passages of elk and between 1 and 3 passages of roe deer each day were observed. During the experimental periods, an average of 1 passage of elk each day was never exceeded. In no instance had the animals followed the entire road section, which was frequently the case during the control periods.

EXAMPLE V

This experiment was conducted in an area having a dense elk population, and as in Example IV, a gravelled forest road was used. The length of the experimental period was 10 days as in Example IV, the control period being 4 days.

Repellent units prepared from extraction sleeves as in Examples I to IV were used. The sleeves were impregnated with the following steroid combinations:

(a) 10 mg androsterone and 10 mg dehydroepiandrosterone (b) 1 mg androsterone and 20 mg testosterone (c) 100 mg dehydroepiandrosterone and 5 mg 11-ketoaetiocholanalone (d) 0.1 mg androsterone and 60 mg iso-androstanalone (e) 25 mg androsterone and 25 mg androstenol (f) 30 mg testosterone, 10 mg dehydroepiandrosterone and 0.05 mg oestrone.

In the experimental periods with the combinations (a) and (c) there were no passages of elk, whereas up to one passage of elk each day was observed with the remaining steroid combinations.

In the control periods between the experiments between 4 and 7 passages of elk each day occurred.

EXAMPLE VI

In these experiments the repellent units were manufactured from conical aluminum sleeves having an inner coating of cellulose. The cellulose coating was impregnated with acetone solutions of various steroid mixtures as indicated below.

An orchard situated in a distinct having a very dense population of roe deer and being pested by roe deer browsing on the fruit trees, was used as an experimental area.

Before the experimental series was started, an average number of 6 roe deer each night visiting and browsing in the orchard was recorded by observation of track prints in the soft ground. The repellent units were suspended at intervals of 7 m around the orchard and approximately 1.5 m above the ground. Observations of track prints were made each morning. Each evening the ground surface was raked to facilitate observation of any track prints.

TABLE I

| Experiment | Steroid mixture | mg in each unit | Experimental period days | Total number of roe deer in the period |
|---|---|---|---|---|
| g | cortisone | 10 | 3 | 1 |
|   | progesterone | 10 |   |   |
| h | none |   | 4 | 18 |
| i | corticosterone | 5 | 8 | 0 |
|   | androsterone | 5 |   |   |
|   | 11α-desoxy-cortisol | 5 |   |   |
| j | none |   | 4 | 21 |
| k | corticosterone | 5 | 8 | 0 |
|   | 11α-desoxy-cortisol | 5 |   |   |
|   | cortisone | 5 |   |   |
|   | progesterone | 2 |   |   |
| l | none |   | 4 | 16 |
| m | androstenol | 1 | 8 | 3 |
|   | cortisone | 10 |   |   |
|   | corticosterone | 10 |   |   |
| n | none |   | 4 | 19 |
| o | prednisolone | 10 | 8 | 1 |
|   | oestriol |   |   |   |
|   | 21-desoxy-cortisone | 3 |   |   |
|   |   | 5 |   |   |

EXAMPLE VII

This experiment was conducted in order to study the long term effect of the repellent substance. An orchard situated on an island surrounded by open water the year round was chosen as an experimental area. A large population of roe deer and a smaller population of hart were present on the island. The total damage on fruit trees and other useful plants by the animals was very extensive. Because of the isolated situation of the island, it may be presumed that no, or at most sporadic, communication with other populations of deer and hart occurs.

The repellent units were shaped in the same manner as described in Example VI, i.e. they consisted of conical cellulose sleeves having an inner coating of cellulose. The cellulose coating was impregnated with an acetone solution of steroids in such an amount that each repellent unit contained 10 mg dehydroepiandrosterone and 10 mg androsterone.

The repellent units were suspended around the orchard at intervals of about 8 m and approximately 1.5 m above the ground. Except for shorter control periods, the experiment lasted for 18 months, which involved that a new generation of animals experienced the repellent substance and that it should be possible to observe any familiarization effects.

The experimental area was inspected every day for trace of deer and hart. Depending on the time of the year, it was possible to observe traces either as track prints in snow or loose soil or as fresh browsing damages on trees. Four control periods of one week each were included in the experimental period. During the control periods all the repellent units were removed. During all the four control periods, numerous visits of deer and hart could be observed already the first night.

During the experimental periods, in which the repellent units were suspended, no visits of deer and hart were observed with the following exceptions:

Days 48 to 50: Visits of 2 to 3 animals each night. During this period there was heavy wind with a wind force of between 15 and 25 m/s, and some of the repellent units were destroyed. After the weather had improved and the damaged units replaced, the protection was again effective.

Day 63: One animal entered, but the track prints showed that the animal had quickly turned around and returned the way it entered.

Days 92 to 96: Traces of one animal were found each morning. A closer inspection disclosed that the animal concerned was a lonely one year old roe fawn which seemed to be hurt. The animal was killed and an examination of the body showed that one of the legs was heavily damaged by shot.

Days 207 to 212: Visits by several animals each night. During this period there was heavy wind and snowfall, and the number of animals was consequently difficult to ascertain.

Days 369 to 370: Visits by one and two animals respectively. External reasons why the animals had entered could not be determined.

Day 486: One animal had entered and according to the track prints, it had run back and forth whereupon it had left the area in long leaps.

During the entire experimental period, animals and traces of animals could be observed in the vicinity of the experimental area. Traces could be observed as close as 25 m from the suspended repellent units.

EXAMPLE VIII

The following animal repellent formulation is prepared:

| Ingredients | Parts by Weight |
|---|---|
| Androsterone having the structure: 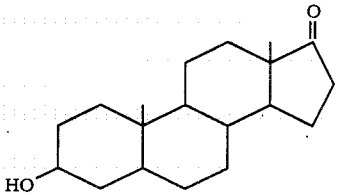 | 18 |
| Dehydroepiandrosterone having the structure: 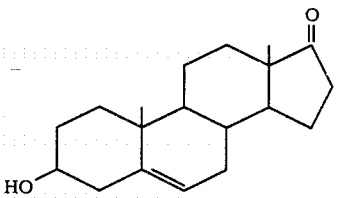 | 18 |

75 pounds of polyethylene prepared according to the procedure of Example I of U.S. Pat. No. 4,370,458 issued on Jan. 25, 1983 (the specification of which is incorporated herein by reference) are heated to about 180° C. in a container of the kind illustrated in FIGS. 8 and 9. Twenty-five pounds of the formulation as set forth above is then quickly added to the liquified polyethylene, the lid 228 is put in place and the agitating means 273 are actuated. The temperature is then raised to about 225° C. and the mixing is continued for 5–15 minutes. The valve "V" is then opened to allow the flow of the molten polyethylene enriched with the steroid material to exit through the orifices 234. The liquid falling through the orifices 234 solidifies almost instantaneously upon impact with the moving cooled conveyor 238. Polyethylene beads or pellets 244 having the steroid contained therein are formed. Analysis demonstrates that the pellets contain about 25% of the steroid formulation so that almost no losses in the steroid material did occur. These pellets may be called "master pellets".

Fifty pounds of the steroid-containing master pellets are then added to 1000 pounds of polyethylene and the mass is heated to the liquid state. The liquid is molded into thin sheets of films. The thin sheets of films (0.01 inches in thickness . . . 10 mils) have pronounced animal repellent effects, particularly in non-predatory elk, roe deer and rabbits. The sheets of films are cut into strips 0.25" in width ×3" in length and placed into articles illustrated in FIGS. 10, 11 and 12. The strips are used in place of the beads in the cylinder as illustrated in FIGS. 10, 11 and 12.

On operation of the apparatus as is shown in Examples IC, et seq., the articles exhibit excellent animal repellency.

EXAMPLE IX(A)

STEROID REPELLENT TEST, FIELD I

Location: The island Byre, southwest Norway, east of Stvanger.

The island has a dense population of roe deer, estimated to be about 50 individuals in one square kilometer. The usual damage: orchards by browsing or antler-rubbing throughout most of the year.

Three field tests were used in the years 1981 and 1982, all of them orchards (apples, pears). The fields are designated 9A, 9B and 9C.

Three different designs of repellents have been tested:

Design I, extraction cylinders as shown in FIGS. 10, 11 and 12 and as produced in Example VIII.

Design II, aluminum-lined cones (ice cream model) and as illustrated in FIGS. 1F and 1G.

Design III, micropore polyethylene film strips (produced using the apparatus of FIG. 2) and used as illustrated in FIGS. 1B and 1C.

In all tests reported here the steroid mixture has been equal parts of androsterone and dehydroepiandrosterone.

Field IXA

About 6000 square meters, mainly apple trees. Before any experiments started, this orchard was regularly visited every night by 3-5 animals. The owner of this orchard is a keen observer and is normally able to trace the movement of the animals in or near the orchard on his daily patrols. Like observers in other fields, he is able to distinguish between fresh and older browsing cuts. The events and observations in this field test are as follows:

10.2.81 Steroid repellents, Design I, were hung in the trees around the orchard, about 1.5 meters above the ground. Distance between repellents 5-12 meters. No intrusions of animals reported between 10.2 and 14.3.

14.3.81 Sleet and snow, followed by cold weather for several days. Intrusion all nights until 20.3.

20.3.81 All repellents removed, dried indoors and replaced. No intrusions reported until 21.4.

21.4.81 All repellents removed. Intrusion and browsing damages by several animals registered next morning. Repellents put back again after one day. No intrusions reported until 27.4.

27.4.81 Heavy rains. Intrusion of several animals. Repellents dried indoors, after which they regained their repellency. No intrusions recorded until 7.5.

7.5.81 All repellents replaced with new repellents, Design II. Except for single incidents in heavy rains, no intrusions were reported until 28.9.

28.9.81 Stormy weather with heavy rains. Many repellents destroyed. Intrusion of "many" animals reported. All repellents were replaced by new ones, also of Design II. No intrusions reported until 5.10.

5.10.81 Heavy rains. Intrusion of several animals reported.

26.10.81 A lonely calf has often been observed inside the line of repellents.

30.10.81 Very strong winds. Most repellents destroyed or blown away. Several animals intruded. The repellents were replaced with new ones of the same design.

4.11.81 The lonely calf shot. Had only 3 legs.

23.11.81 New storm. Most repellents damaged. Invasion of sevreral animals most nights for a week, when new repellents were installed.

4.1.82 Sleet and snow. Intrusion of some animals. After drying indoors, the repellents seemed effective until 7.1.

7.1.82 Temperature −12° C. Intrusions. When the temperature rose after a few days, no animals intruded.

13.1.82 A cold period. Intrusions reported when temperatures were below −8° C.

13.4.82 All repellents removed. "Many" animals intruded.

14.4.82 New repellents Design II. No intrusions reported until 11.5.

11.5.82 All repellents removed for one night. Several animals intruded. When the repellents were returned no intrusions were reported until 19.6.

19.6.82 New repellents, Design III, were introduced. One corner of the orchard was reserved for blank film repellents without steroids.

28.6.82 No intrusions in the part of the orchard protected with real Design III repellents. Several intrusions were reported in the corner "protected" by blanks. The owner of the orchard was not informed that some of the repellents were blanks. The blanks were replaced by repellents of Design II, identical with those introduced 14.4.

23.8.82 No intrusions have been reported in the part of the orchard protected with Design III repellents. Two calves have continued to visit now and then the Design II protected area.

8.10.82 Strong wind and heavy rains. Intrusions in Design II area, no intrusions in Design III area.

22.10.82 Strong wind and heavy rains. Same observations as 8.10.

15.11.82 Heavy rains. Observations as 8-22.10.

30.11.82 All Design II repellents replaced with Design III.

28.12.82 No new observations of intrusion. Since 19.6 most of the orchard has been protected by repellents of Design III. The same repellents have been used all the time. No intrusions have been reported in this period.

The summer 1982 has been exceptionally dry (May, June and July) and warmer than usual. November and December have been mild for the time of the year with a few days with temperatures below 0° C.

Concentrated hunting in the days before Christmas 1982 elsewhere on the island has drastically reduced the deer population.

Field IXB

This orchard is about 2000 square meters and is situated 150 meters from Field IXA. Before the repellent tests in Field IXA started, this orchard was regularly visited by 1-3 roe deer per night. When the tests in Field IXA had continued for some time, the number of intruding animals in Field IXB increased.

At the request of the owner of Field IXB, repellents of Design II were June 17, 1981 hung around his orchard in the same pattern as in Field IXA. The results have been more or less the same as in Field IXA, but the owner of this orchard is not as diligent an observer as the owner of Field IXA. Our reports from Field IXB are therefor not as comprehensive as those from Field IXA.

When destroyed by storm and rains, the repellents have been replaced by new ones as in Field IXA. Only 5 intrusions in Field IXB were reported until July 1, 1982. On this date the Design II repellents along 150 m of the orchard were replaced with blanks of Design III. In the following 3-4 nights several animals intruded and caused considerable browsing damage. The owner demanded that the original repellents should be put back. This was done.

On Nov. 30, 1982, all repellents of Design II were replaced by Design III repellents. No intrusions reported until 28.12.1982.

Field IXC

An orchard with newly planted trees. About 1500 square meters, situated 200 meters from Field IXA. Same owner as Field IXA. This orchard was included in the field tests on the insistence of the owner who wanted protection for his new trees. Therefor no "blank" periods have been applied.

8.2.82 Steroid repellents, Design II applied around the orchard in normal pattern. No intrusions reported until 3.5.

3.5.82 All repellents replaced with a new version of Design II, where another solvent for the steroids was tested. Steroid mixture same as before.

8.10.82 Strong wind and heavy rains. One animal had passed through the field. No browsing damage observed.

22.10.82 Strong and heavy rains. Two or three animals intruded, but no damage registered.

15.11.82 Heavy rains. Observations as 22.10.82.

30.11.82 All Design II repellents replaced with Design III. No reports on intrusions until 28.12.82.

EXAMPLE IX(B)

STEROID REPELLENT TEST, FIELD 2

Tuftene, 10,000 square meter orchard on the mainland east of Stavanger. Dense population of roe deer. Up to 6 animals have been reported to invade the orchard in one night. One doe with two calves can be seen from the windows of the living house daily, even in daytime.

7.07.81 Steroid repellents Design II were hung in trees on three sides of the orchard. No detectable damage was done in the orchard, and no observations of intruding animals were made until 18.11. On several occasions the doe with the two calves was seen approaching the repellent line, but always turning back.

18.11.81 Strong wind and heavy rain. Intrusion of several animals registered. The repellents were partly destroyed by the storm.

19.11.81 New repellents were installed. No intrusions registered until 14.12.

14.12.81 From 14.12 until 23.12 cold weather prevailed, $-5°-10°$ C. Intrusions were registered most nights.

23.12.81 Mild weather (0° C.) until 01.01.82. No intrusion observed.

01.01.82 A new period with cold weather until 13.01. Intrusion of several animals registered most days.

13.01.82 Varying weather conditions with fluctuating temperatures until 05.03. The reports seem to indicate that intrusion was normal in nights with temperatures around $-5°$ C.$--10°$ C.

05.03.82 All repellents replaced with new ones, also of Design II. No intrusions until 05.04. The observers have noted that the animals seem to turn away from the repellent line at a distance of about 40 m in normal weather, while on rainy days they approach to about 10 m.

05.04.82 All repellents removed for one night. Several animals intruded. When repellents were replaced, no intrusions were observed until 03.05.

03.05.82 All repellents removed for one week. Several animals intruded all nights.

11.05.82 Repellents put back. No intrusions reported for several months.

07.09.82 Repellent effect seems to be decreasing. For the last few weeks intrusions are reported now and then. The same repellents have been used for 6 months (since 05.03.82). All repellents replaced with new ones of the same design. (Design II) Until 08.10 no intrusions reported.

08.10.82 Strong wind and rains. Two animals intruded.

22.10.82 Strong wind and rains. Three animals intruded.

30.11.82 All repellents replaced with Design III. No report of intrusions until 29.12.82. All of December has had mild weather.

EXAMPLE IX(C)

STEROID REPELLENT TEST, FIELD 3

Joseneset. Situated on the mainland east of Stavanger. Red deer invades the area, normally from beginning of September. The animals will stay until early spring. The population is estimated to approximately 15 animals of both sexes and of diferent age groups.

The test field consisted of cauliflower and strawberry plantations, both species popular in the diet of red deer.

17.09.81 The repellents, Design II, were installed in the normal pattern in the strawberry field and in one cauliflower field. 2-3 animals had been observed 10.09, and the number increased to 10-15 animals in a week. Some browing damage was registered before the repellents were installed. No intrusions were observed until 13.10. Some animals continued most nights to approach the fields along their normal paths, but turned around 10-15 m from the repellents. This could be ascertained by tracing the footprints of the animals.

13.10.81 Storm and rains destroyed most of the repellents. The following night 8-10 animals had invaded the test field. The instrusion was repeated even the next night.

15.10.81 New repellents were installed instead of those destroyed by the storm. No intrusions reported until 14.11.

14.11.81 One male deer had entered the field from the unprotected side, close to the living house of the farm. After some confused running around it had left the same way, apparently without doing any browsing damage.

30.11.81 Another storm destroyed most repellents.

23.12.81 New repellents were installed. Between 23.12.81 and 01.01.82 the animals were not observed or registered in the area. They returned 01.01.82. A cold period prevailed until 13.01. Temperature $-6°$ to $-10°$ C. The animals intruded most nights.

13.01.82 Mild weather. No intrusions reported for the rest of the winter. The test was discontinued when the animals left the area in March.

EXAMPLE IX(D)

STEROID REPELLENT TEST, FIELD 4

Landsnes. Situated on the mainland east of Stavanger. An orchard with mostly pear trees, and a garden nursery. A heard of red deer has caused damage through most of the year. Browsing and antler-rubbing.

20.03.81 A line of repellents, Design II, were hung in the normal pattern around both the orchard and the nursery. Until 20.05 no intrusions had occurred in the orchard, although footprints showed that the animals on most nights had approached the repellent line. After 20.05 no animals or footprints were observed near the orchard. Animals were observed regularly close to the nursery until the end of August. No damage was registered.

28.09.81 Strong wind with rain. Intrusion one night.
30.10.81 Intrusion one night. The repellents were exchanged with new ones of same design. No intrusions until 16.11.
16.11.81 Strong wind. Two animals intruded one night.

This test has continued into 1982 with no reports of deer intrusion. However, few animals have been observed in the area in this period. Continued testing is therefore of no value.

EXAMPLES IX(E) AND (F)

STEROID REPELLENT TEST, FIELDS 5 AND 6

Ombo and Skartveit. Islands east of Stavanger. Both these field tests commenced late September 1981 with repellents of Design II.

Reports from these fields have been very irregular and with poor documentation. In both fields roe deer was the main problem and the general experience is the same as reported from other fields.

The repellent effect is good except in cold weather and in heavy rain with strong wind.

EXAMPLE IX(G)

STEROID REPELLENT TEST, FIELD 7

Ullensvang, situated at a fjord on the west coast. Main problem red deer and roe deer.

Field No. 7A

An orchard, mainly apple trees. The trees in this orchard were planted in 1981. Browsing damage by roe deer were reported during the spring 1982.

Repellents of Design II were installed in the normal pattern on July 30.82. The plantation was inspected every 10 days. In the period 10-14 August, browsing damage was registered. Heavy rains were registered in these days, 22,3 mm on 10.8 and 34,0 mm on 12.8.

After this period no damage has been registered until October 1 the date of the last written report.

Field No. 7B

Plantation of apple trees and strawberries. A herd of 12 red deer was observed in the area. On these nights before the repellents were installed (21.8.82) red deer had visited the plantation causing considerable browing damage.

After the repellents were installed, footprints of the herd could be traced to within 20 meters from the repellent line, were the animals had turned around.

Later in the summer, the animals have not been observed in the area. No new damage registered until October 1.

In December 1982 repellents of Design III have been installed in both fields.

EXAMPLE IX(H)

STEROID REPELLENT TEST, FIELD 8

Bo in Telemark. Central Norway. Moose, roe deer, hare and beaver. Plantation with apple trees, strawberries and vegetables. As a separate field, barley.
February, 1982 Repellents of Design II installed in the orchard, strawberry field.
03.03.82 No damage reported, no intrusions reported until 10.08.
10.08.82 The observations indicate that the repellents have been effective against moose in the warm July-August period. Moose normally cause considerable damage in barley fields in this area.
23.08.82 Heavy rains. Two moose intruded. No intrusions by roe deer.
30.08.82 Repellents of Design III were installed in part of the field. Believed to have effect against moose but not against beaver.
13.09.82 Roe deer reported to turn away 50-60 meters from the repellent line.
06.12-82 All repellents removed. New repellents of Design III installed. No intrusions observed until 14.12. Roe deer and hare reported in the area.
14.12.82 Cold weather. Repellents covered by frost. Roe deer and hare have intruded.
20.12.82 Milder temperatures. No intrusions by hare or roe deer. On days with temperatures $-5°--10°$ C. both hare and roe deer intruded.

EXAMPLE X

STEROID REPELLENT TEST, FIELDS 9 & 10

Varmland in Sweden. Moose and roe deer browsing in oat fields.

Field 9

15 acres oat plantation. Repellents of Design IV as illustrated and used as illustrated in FIGS. 1D and 1F installed 5.08.81 (82 units) containing 1:1 (mole ratio) of dehydroepiandrosterone and androsterone.
12.08.81 1 moose calf intruded.
18.08.81 No intrusions reported since 12.08.
27.08.81 No intrusions reported. Roe deer have been observed 20-30 meters from repellents.
02.09.81 Both moose bulls and cows reported browsing. Roe deer have not intruded.
09.09.81 The field harvested. The last days moose cow with calf, bulls and yearlings have intruded.

The damage in the oat field evaluated officially to 15%. The 1980 damage was 50%. The main reason for the reduced damage is believed to be the absence of roe deer. In 1980, 15-18 roe deer regularly visited the field.

Field 10

65 acres oat plantation. 108 repellent units installed 05.08.81 (Design IV).
12.08.81 2 moose cows and 3 calves intruded.
18.08.81 No new intrusions of moose.
19.08.81 "Many" moose intrude.
21.08.81 150 new repellents installed along the border of the surrounding wood and in the middle of the field.
24.08.81 Intrusion by several animals.
27.08.81 Intrusions by moose every night.
09.09.81 The field harvested. The official evaluation of damage gave 25 and 30% for different parts of the field. Neighboring fields had 50% damage, the same as "our" field had in 1980. No roe deer were observed in the field during the test. No roe deer were felled during the first part of the hunting season in September. In 1980 6 deer were felled in the same period.

EXAMPLE XI

During December 1980/January 1982 preliminary field tests with steroid combinations were conducted. The test sites were the same as in Field test I in Example IX supra. Repellents were of Design I (extraction cylinders). In the first series three combinations of steroids were tested.
Combination 1:

10 mg testosterone
10 mg eticholanolone

Combination 2:
10 mg dehydroepiandrosterone
10 mg androsterone

Combination 3:
10 mg androstendione
10 mg progesterone

Only combination 2 had effect. Roe deer intruded all nights for a week with combinations 1 and 3.

The second series were conducted with repellent units impregnated with dehydroepiandrosterone alone (10 mg) and androsterone along (10 mg). The tests were negative. Also negative were combinations of eticholanolone/androsterone and eticholanolone/dehydroepiandrosterone.

In August 1981, a series of tests with repellents impregnated with 2.5, 5, 7 and 10 mg of each of the steroids from combination 2 was conducted. The results were inconclusive as could be expected. Our evaluation method is not suited for quantitative comparisons, as we only get a "yes" or "no" answer.

In October 1981 repellents impregnated with 5 mg each of androsterone, dehydroepiandrosterone, testosterone and androstendione were tested in Sweden against moose. Results closely similar to those obtained when using repellents with only androsterone and dehydroepiandrosterone were obtained.

The same can be said for a test in Norway in June 1982 with a combination of 10 mg each of dehydroepiandrosterone, androsterone, cortisone, corticosterone and progesterone.

The term "steroids" may seem comprehensive but this is not true with regard to the fact that the steroids of our case form a very well defined group of chemical compounds having common basic structure; structure:

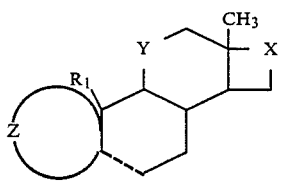

wherein X completes a substituted cyclopentyl moiety and is one of the moieties:

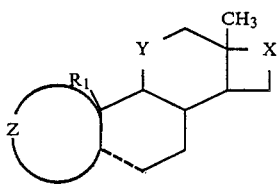

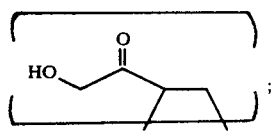

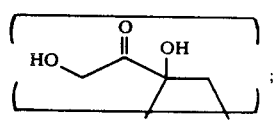

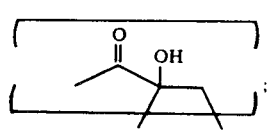

-continued

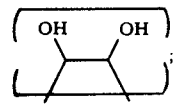

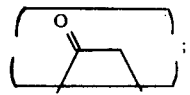

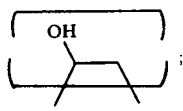

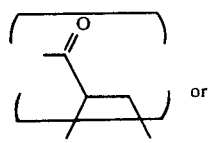 or

wherein Y represents methylene, carbinol or keto; and wherein Z completes a substituted cyclohexyl moiety which is, in the alternative:
hydroxycyclohexyl;
ketocyclohexyl;
ketocyclohexenyl;
hydroxyphenyl;
cyclohexenyl; or
bicyclohexyl and wherein the dashed line represents a carbon-carbon single bond or a carbon-carbon double bond and varying only slightly as far as substituents and double bonds are concerned. The steroids used in these experiments have been carefully selected in order to form a representative selection of the group of substances defined in the claims.

As is apparent from the claims, the invention is restricted to the use of individual or a small number of steroids at a time. The steroids used are synthetic or extracted from naturally occurring materials by any suitable chemical or physical isolation process.

What is claimed is:

1. A method for repelling non-predatory animals by placing smelling repellent substances in the area from which the animals are to be kept off characterized by the use as a repellent substance of one or more steroids defined according to the structure:

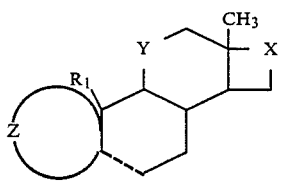

wherein X completes a substituted cyclopentyl moiety and is one of the moieties:

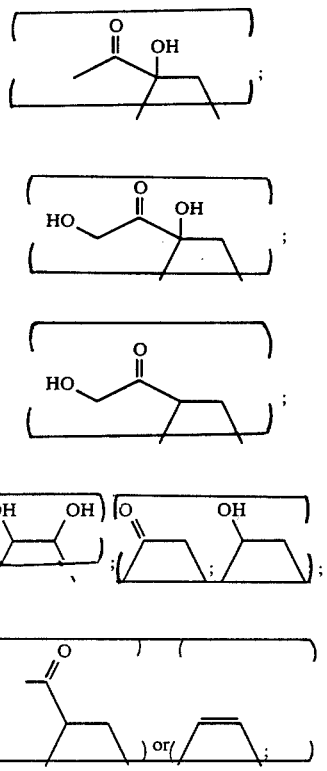

wherein Y represents methylene, carbinol or keto; and wherein Z completes a substituted cyclohexyl moiety which is, in the alternative:
hydroxycyclohexyl;
ketocyclohexyl;
ketocyclohexenyl;
hydroxyphenyl;
cyclohexenyl; or
bicyclohexyl
and wherein the dashed line represents a carbon-carbon single bond or a carbon-carbon double bond, which steroids are synthetic or have been extracted from naturally occurring materials and which are of the type occurring on human skin or hair or in human sweat or urine and/or of one or more of the derivatives thereof obtainable by subjecting the steroids to air, moisture or microorganisms in such a manner as to provide in the air a concentration perceptible to the sense of smell of the non-predatory animals.

2. A process according to claim 1 characterized by the use as a repellent substance of a mixture of two or more steroids or steroid derivatives.

3. A process according to claim 1 characterized by the use as a repellent substance of a steroid selected from the group consisting of testosterone, androsterone, dehydroepiandrosterone, 11-keto-etiocholanalone, isoandrostanalone, estrone and androstenol.

4. A method according to claim 1 characterized by placing one or more repellent units on or at the borders of the area from which it is desired to repel the animals.

5. A method according to claim 4 characterized in that the amount of repellent substance for each repellent unit is at least 1 nanogram and preferably between 0.1 µg and 100 mg.

6. A method according to claim 1 characterized by the use as a repellent substance of androsterone or dehydroepiandrosterone or mixtures comprising androsterone and dehydroepiandrosterone.

7. A method according to claim 2 characterized by the use as a repellent substance of steroids selected from the group consisting of testosterone, androsterone, dehydroepiandrosterone, 11-keto-etiocholanalone, isoandrostanalone, estrone and androstenol.

8. Method according to claim 2 characterized by placing one or more repellent units on or at the borders of the area from which it is desired to repel the animals.

9. Method according to claim 3 characterized by placing one or more repellent units on or at the borders of the area from which it is desired to repel the animals.

10. Method according to claim 5 characterized by the use as a repellent substance of androsterone or dehydroepiandrosterone or mixtures comprising androsterone and dehydroepiandrosterone.

11. The method of claim 1 wherein the repellent substance is embedded in a polymer.

12. The method of claim 1 wherein the animals repelled are of the Cervidae family.

13. The method of claim 12 wherein the members of the Cervidae family are selected from the group consisting of elk and roe deer.

14. The method of claim 1 wherein the non-predatory animals repelled are of the genus Leporidae.

15. The process of claim 14 wherein the members of the genus Leporidae are selected from the group consisting of hare and rabbits.

* * * * *

UNITED STATES PATENT AND TRADEMARK OFFICE
CERTIFICATE OF CORRECTION

PATENT NO. : 4,534,976  
DATED : August 13, 1985  
INVENTOR(S) : Helge Hansen, Borje Nystrom and Eyvin Torneng It is certified that error appears in the above-identified patent and that said Letters Patent are hereby corrected as shown below:

Cover page of U.S. Letters Patent 4,534,976, left-hand column, item (73) Assignee:, replace "International Flavors & Fragrances Inc., New York, N.Y." with:

---Nordtend A/S, a corporation of Norway located in Stavanger, Norway---

Cover page of U.S. Letters Patent 4,534,976, right-hand column, lines 7 and 8, replace lines 7 and 8 with:

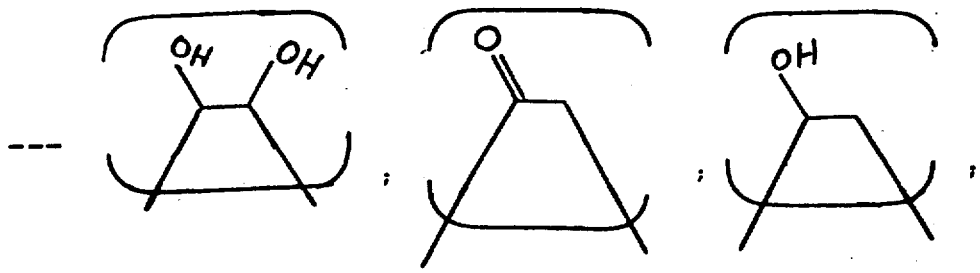

UNITED STATES PATENT AND TRADEMARK OFFICE
CERTIFICATE OF CORRECTION

PATENT NO. : 4,534,976

DATED : August 13, 1985

INVENTOR(S) : Helge Hansen et al.

It is certified that error appears in the above-identified patent and that said Letters Patent is hereby corrected as shown below:

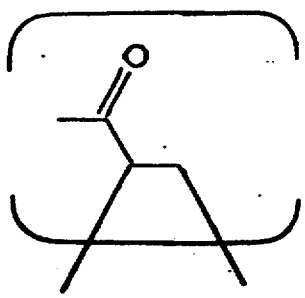 or 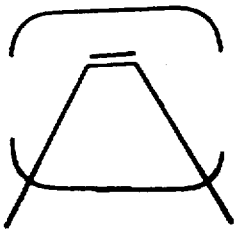 ;

Signed and Sealed this

Twenty-sixth Day of November 1985

[SEAL]

Attest:

DONALD J. QUIGG

Attesting Officer       Commissioner of Patents and Trademarks